US006919073B2

(12) United States Patent
Legrand et al.

(10) Patent No.: US 6,919,073 B2
(45) Date of Patent: Jul. 19, 2005

(54) PULVERULENT COMPOSITION FOR BLEACHING HUMAN KERATIN FIBERS

(75) Inventors: Frédéric Legrand, Courbevoie (FR); Jean-Marie Millequant, Saint-Maur des Fosses (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 10/146,030

(22) Filed: May 16, 2002

(65) Prior Publication Data

US 2003/0078330 A1 Apr. 24, 2003

(30) Foreign Application Priority Data

May 16, 2001 (FR) .............................................. 01 06461

(51) Int. Cl.$^7$ .............................................. A61K 7/135
(52) U.S. Cl. ........................ 424/62; 424/701; 132/208
(58) Field of Search ........................ 424/62, 70.1, 701; 132/208

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,528,378 A | 10/1950 | Mannheimer |
| 2,781,354 A | 2/1957 | Mannheimer |
| 2,961,347 A | 11/1960 | Floyd |
| 3,206,462 A | 9/1965 | McCarty |
| 3,227,615 A | 1/1966 | Korden |
| 3,632,559 A | 1/1972 | Matter et al. |
| 3,836,537 A | 9/1974 | Boerwinkle et al. |
| 3,874,870 A | 4/1975 | Green et al. |
| 3,915,921 A | 10/1975 | Schlatzer, Jr. |
| 3,917,817 A | 11/1975 | Vanlerberghe et al. |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,131,576 A | 12/1978 | Iovine et al. |
| 4,157,388 A | 6/1979 | Christiansen |
| 4,172,887 A | 10/1979 | Vanlerherghe et al. |
| 4,223,009 A | 9/1980 | Chakrabarti |
| 4,277,581 A | 7/1981 | Vanlerberghe et al. |
| 4,349,532 A | 9/1982 | Vanlerberghe et al. |
| 4,509,949 A | 4/1985 | Huang et al. |
| 4,591,610 A | 5/1986 | Grollier |
| 4,608,250 A | 8/1986 | Jacquet et al. |
| 4,702,906 A | 10/1987 | Jacquet et al. |
| 4,719,099 A | 1/1988 | Grollier et al. |
| 4,719,282 A | 1/1988 | Nadolsky et al. |
| 4,761,273 A | 8/1988 | Grollier et al. |
| 4,839,166 A | 6/1989 | Grollier et al. |
| 4,996,059 A | 2/1991 | Grollier et al. |
| 5,139,037 A | 8/1992 | Grollier et al. |
| 5,196,189 A | 3/1993 | Jacquet et al. |
| 5,622,691 A | 4/1997 | Tricaud et al. |
| 5,660,190 A | 8/1997 | Tricaud et al. |
| 6,260,556 B1 * | 7/2001 | Legrand et al. .............. 132/208 |

FOREIGN PATENT DOCUMENTS

| | | | |
|---|---|---|---|
| DE | 199 43925 | * | 5/2000 |
| EP | 0 080 976 | | 6/1983 |
| EP | 0 663 205 | | 7/1995 |
| FR | 2 077 143 | | 10/1971 |
| FR | 2 080 759 | | 11/1971 |
| FR | 2 320 330 | | 3/1977 |
| FR | 2 336 434 | | 7/1977 |
| FR | 2 633 940 | | 1/1990 |
| FR | 2 788 976 | | 8/2000 |
| WO | WO 98/44012 | | 10/1998 |

OTHER PUBLICATIONS

Porter et al., "Handbook of Surfactants", Glasgow & London, 1991, pp 117–178.

G. Fonnum et al., "Associative thickeners. Part I: Synthesis, rheology and aggregation behavior," Colloid & Polymer Science, vol. 271, No. 4, Apr. 1993, pp 380–389.

William C. Griffin, "Calculation of HLB Values of Non-Ionic Surfactants," The Journal of the Society of Cosmetic Chemists, vol. V, No. 2, Jun. 1954, pp 249–256.

English language Derwent Abstract of DE 199 43 925, May 18, 2000.

English language Derwent Abstract of EP 0 080 976, Jun. 8, 1983.

(Continued)

Primary Examiner—Jyothsna Venkat
(74) Attorney, Agent, or Firm—Finnegan, Henderson, Farabow, Garrett & Dunner LLP

(57) ABSTRACT

A pulverulent composition for bleaching human keratin fibers, such as hair, comprising at least one peroxygenated salt, at least one polymer chosen from nonionic and anionic amphiphilic polymers, wherein the at least one polymer comprises at least one fatty chain; and less than 10% by weight of a fatty acid sugar ester comprising at least one sugar residue and at least one $C_{12}$–$C_{24}$ fatty acid residue. The pulverulent composition is capable of being mixed with at least one aqueous hydrogen peroxide composition having a titer of not more than 40 volumes to form stable, homogeneous, bleaching compositions that can be applied precisely and easily, and can produce a homogeneous bleaching of the hair that does not leave the hair coarse.

21 Claims, No Drawings

OTHER PUBLICATIONS

English language Derwent Abstract of FR 2 077 143, Oct. 15, 1971.
English language Derwent Abstract of FR 2 080 759, Nov. 19, 1971.
English language Derwent Abstract of FR 2 320 330, Mar. 4, 1977.
English language Derwent Abstract of FR 2 336 434, Jul. 22, 1977.
English language Derwent Abstract of FR 2 633 940, Jan. 12, 1990.
English language Derwent Abstract of FR 2 788 976, Aug. 4, 2000.

* cited by examiner

PULVERULENT COMPOSITION FOR BLEACHING HUMAN KERATIN FIBERS

The present invention relates to a pulverulent composition for bleaching human keratin fibers, such as hair, comprising, in a medium that is suitable for bleaching: at least one peroxygenated salt; at least one amphiphilic polymer chosen from nonionic amphiphilic polymers and anionic amphiphilic polymers, wherein the at least one amphiphilic polymer comprises at least one fatty chain; and less than 10% by weight of a fatty acid sugar ester comprising at least one sugar residue and at least one $C_{12}$–$C_{24}$ fatty acid residue. The invention also relates to the use of the pulverulent composition, or powder, for the preparation of a composition for bleaching human keratin fibers, to a process for preparing the said powder, and to a process for bleaching keratin fibers.

Human keratin fibers, such as hair, are bleached by oxidizing the "melanin" pigment, resulting in the dissolution and partial or total removal of this pigment.

To bleach the hair, it is known to use bleaching powders, which may contain a peroxygenated reagent such as ammonium or alkali metal persulphates, perborates and percarbonates, which are combined at the time of use with an aqueous hydrogen peroxide composition.

Because peroxygenated salts and hydrogen peroxide are relatively stable in acidic medium, it may often be necessary to activate them at basic pH to obtain an adequate formation of oxygen. It is thus common practice to add to bleaching powders alkaline compounds such as urea, alkali metal silicates, such as alkali metal metasilicates, alkaline-earth metal silicates, phosphates or carbonates, and ammonia precursors, such as ammonium salts.

In haircare cosmetics, this aqueous hydrogen peroxide composition should not have a titre of more than 40 volumes.

However, in hairdressing salons, in order to increase the bleaching performance of pulverulent bleaching compositions, certain hair stylists might be tempted to use aqueous hydrogen peroxide solutions that are not formulated for cosmetic use and that have a titre of more than 40 volumes. These practices can be dangerous and could jeopardize the client's comfort and safety.

Thus, there remains a need for a novel bleaching powder that can be used with aqueous hydrogen peroxide compositions at volumes of less than 40 volumes.

It is known that bleaching powders have a tendency to form dust during their handling, transportation and storage. Given that the compounds of which bleaching powders are composed (alkali metal persulphates and silicates) may be corrosive and irritant to the eyes, the respiratory pathways and mucous membranes, it has been proposed to reduce dust content by depositing on the powder, by means of a spraying process, various compounds that are substantially insoluble in water, such as, for example, oils or liquid waxes, which, by coating the powder particles, aggregate them into particles of coarser size. European Patent EP 560 088 describes such a process.

To reduce dust content, it has also previously proposed to use liquid anhydrous polymers that are soluble in water at room temperature, such as those chosen from polyethylene glycols or polypropylene glycols (French patent No. 2 716 804), or block and/or random block linear polymers of the type such as polyoxyethylene/polyoxypropylene (European Patent EP 663 205).

In German patent application DE 199 43 925 A1, fatty acid sugar esters have been proposed to reduce dust content.

Moreover, in order to localize the bleaching product on the hair so that it does not run down the face or outside the areas that are intended to be bleached, it is known to thicken or gel the bleaching compositions with conventional thickeners such as water-soluble thickening polymers, for instance cellulose derivatives, starch derivatives, crosslinked polyacrylic acid or alginates or alternatively with thickening silicas.

Because these conventional thickeners may result in a fall in the viscosity of the bleaching compositions over time, it has been proposed, in French patent 2 788 974, to use a thickening system capable of maintaining a high viscosity for the time required to obtain the desired bleaching. This thickening system comprises a combination of a standard water-soluble thickener with a nonionic amphiphilic polymer comprising at least one fatty chain.

However, the bleaching treatment may often be corrosive and can lead to poor cosmetic properties of the hair, such as any one of difficult disentangling, an unpleasant feel, coarse and dull hair, and degradation of the fibers. It has been proposed in French patent No 2 788 976 to limit this degradation by using a combination of nonionic and/or anionic amphiphilic polymers and of cationic or amphoteric substantive polymers.

After considerable research, the inventors have discovered a novel pulverulent composition that can be stable on storage and that can be mixed only with aqueous hydrogen peroxide compositions that have a titre of not more than 40 volumes. The pulverulent composition can form homogeneous, stable, ready-to-use bleaching compositions that can be easy to apply, and that can remain where applied without running or spreading onto the areas of the hair that it is not desired to bleach. The compositions can result in intense and homogeneous bleaching results without rendering the hair coarse.

The inventors have noted that mixtures of the pulverulent compositions according to the invention with aqueous hydrogen peroxide compositions that have a titre of more than 40 volumes were heterogeneous and unstable, did not allow an easy or sufficiently precise application without running, and spread onto areas of the hair that were not intended to be bleached. Moreover, such compositions gave a heterogeneous hair bleaching effect and left the hair coarse.

The novel pulverulent composition according to the present invention may, for example, be anhydrous. This powder may also be non-volatile, i.e., free of dust (or fines). Alternatively stated, the powder can have a particle size distribution where the weight content of the particles less than or equal to 65 microns in size (fines content) is generally less than or equal to 5%. In one embodiment, the weight content of such particles is less than 2%, for example, less than 1%.

One embodiment of the present invention relates to a pulverulent composition for bleaching human keratin fibers, such as hair, comprising, in a medium that is suitable for bleaching, (i) at least one peroxygenated salt, (ii) at least one amphiphilic polymer chosen from nonionic amphiphilic and anionic amphiphilic polymers, the at least one amphiphilic polymer comprising at least one fatty chain, and (iii) at least one fatty acid sugar ester comprising at least one sugar residue and at least one $C_{12}$–$C_{24}$ fatty acid residue, the at least one fatty acid sugar ester being present and in an amount of less than 10% by weight relative to the total weight of the composition. In one embodiment, the at least one fatty acid sugar ester is present in an amount of less than 5% by weight relative to the total weight of the composition, such as an amount ranging from 0.5% to 2% by weight relative to the total weight of the composition.

Another embodiment of the present invention relates to a pulverulent composition for bleaching human keratin fibers, such as hair, comprising, in a medium that is suitable for bleaching, (i) at least one peroxygenated salt, (ii) at least one amphiphilic polymer chosen from nonionic amphiphilic and anionic amphiphilic polymers, the at least one amphiphilic polymer comprising at least one fatty chain, and (iii) at least one fatty acid sugar ester derived from at least one sugar and at least one $C_{12}$–$C_{24}$ fatty acid, the at least one fatty acid sugar ester being present and in an amount of less than 10% by weight relative to the total weight of the composition.

Another embodiment of the invention is a method of preparing a ready-to-use composition for bleaching human keratin fibers. The method comprises mixing, at the time of application, a pulverulent composition with an aqueous hydrogen peroxide composition having a hydrogen peroxide titre of not more than 40 volumes, the pulverulent composition comprising, in a medium that is suitable for bleaching, (i) at least one peroxygenated salt, (ii) at least one amphiphilic polymer chosen from nonionic amphiphilic and anionic amphiphilic polymers, the at least one amphiphilic polymer comprising at least one fatty chain, and (iii) at least one fatty acid sugar ester comprising at least one sugar residue and at least one $C_{12}$–$C_{24}$ fatty acid residue, the at least one fatty acid sugar ester being present and in an amount of less than 10% by weight relative to the total weight of the composition.

For the purposes of the present invention, the expression "ready-to-use composition" means the composition is intended to be applied in unmodified form to the keratin fibers, i.e., it results from the extemporaneous mixing of the powder and of the aqueous hydrogen peroxide composition.

For the purposes of the present invention, the term "anhydrous" means a powder whose water content is less than 5%, such as less than 1%, for example, less than 0.5% by weight.

Another embodiment of the invention relates to a method for bleaching human keratin fibers, such as hair. The method comprises mixing, at the time of application, a pulverulent composition with an aqueous hydrogen peroxide composition having a titre of not more than 40 volumes to produce a bleaching composition, the pulverulent composition comprising, in a medium that is suitable for bleaching, (i) at least one peroxygenated salt, (ii) at least one amphiphilic polymer chosen from nonionic amphiphilic and anionic amphiphilic polymers, the at least one amphiphilic polymer comprising at least one fatty chain, and (iii) at least one fatty acid sugar ester comprising at least one sugar residue and at least one $C_{12}$–$C_{24}$ fatty acid residue, the at least one fatty acid sugar ester being present and in an amount of less than 10% by weight relative to the total weight of the composition. The method also comprises applying the bleaching composition to the keratin fibers; and leaving the bleaching composition on the fibers for an exposure time sufficient to bleach the fibers. The method can further comprise rinsing the bleached fibers. The method can optionally comprise washing the rinsed fibers with shampoo, rinsing the washed fibers, and drying the rinsed fibers.

Yet another embodiment of the invention is a kit for bleaching human keratin fibers comprising at least two compartments. The kit comprises a first compartment, which comprises a pulverulent composition comprising, in a medium that is suitable for bleaching, (i) at least one peroxygenated salt, (ii) at least one amphiphilic polymer chosen from nonionic amphiphilic and anionic amphiphilic polymers, the at least one amphiphilic polymer comprising at least one fatty chain, and (iii) at least one fatty acid sugar ester comprising at least one sugar residue and at least one $C_{12}$–$C_{24}$ fatty acid residue, the at least one fatty acid sugar ester being present and in an amount of less than 10% by weight relative to the total weight of the composition. A second compartment comprises an aqueous hydrogen peroxide composition having a titre of not more than 40 volumes.

Still another embodiment of the invention is a method of preparing a pulverulent composition for bleaching human keratin fibers, comprising mixing, at a temperature of 25° C., at least one fatty acid sugar ester comprising at least one sugar residue and at least one $C_{12}$–$C_{24}$ fatty acid residue, wherein the at least one fatty acid sugar ester is present and in an amount of less than 10% by weight relative to the total weight of the composition, with a mixture comprising at least one peroxygenated salt and at least one amphiphilic polymer chosen from nonionic amphiphilic and anionic amphiphilic polymers, the at least one amphiphilic polymer comprising at least one fatty chain.

Another embodiment of the present invention relates to a ready-to-use composition for bleaching human keratin fibers, comprising: (a) a pulverulent composition comprising, in a medium that is suitable for bleaching, (i) at least one peroxygenated salt; (ii) at least one amphiphilic polymer chosen from nonionic amphiphilic and anionic amphiphilic polymers, the at least one amphiphilic polymer comprising at least one fatty chain; and (iii) at least one fatty acid sugar ester comprising at least one sugar residue and at least one $C_{12}$–$C_{24}$ fatty acid residue, the at least one fatty acid sugar ester being present and in an amount of less than 10% by weight relative to the total weight of the composition; and (b) an aqueous hydrogen peroxide composition having a hydrogen peroxide titre of not more than 40 volumes.

Other embodiments of the invention will emerge even more clearly on reading the description and the examples that follow.

Nonionic Amphiphilic Polymers Comprising at Least One Fatty Chain

Nonionic amphiphilic polymer comprising at least one fatty chain useful in the present invention may be chosen from, but are not limited to:

(1) celluloses modified with groups comprising at least one fatty chain, such as, for example:
   hydroxyethylcelluloses modified with groups comprising at least one fatty chain, such as alkyl, arylalkyl, alkylaryl groups, and mixtures thereof, and in which the alkyl groups may be $C_8$–$C_{22}$, such as the product Natrosol Plus Grade 330 CS® ($C_{16}$ alkyls) sold by the company Aqualon, or the product Bermocoll EHM 100® sold by the company Berol Nobel, and
   celluloses modified with polyalkylene glycol alkylphenyl ether groups, such as the product Amercell Polymer HM-1500® (polyethylene glycol (15) nonylphenyl ether) sold by the company Amerchol;

(2) hydroxypropyl guars modified with groups comprising at least one $C_8$ to $C_{22}$ fatty chain, such as the product Jaguar XC-95/3® ($C_{14}$ alkyl chain) sold by the company Rhodia, the product Esaflor HM 22® ($C_{22}$ alkyl chain) sold by the company Lamberti, and the products RE210-18® ($C_{14}$ alkyl chain) and RE205-1® ($C_{20}$ alkyl chain) sold by the company Rhône-Poulenc;

(3) copolymers derived from vinylpyrrolidone and hydrophobic monomers containing a fatty chain, such as, for example:

the products Antaron V216® or Ganex V216® (vinylpyrrolidone/hexadecene copolymer) sold by the company I.S.P., and the products Antaron V220® or Ganex V220® (vinylpyrrolidone/eicosene copolymer) sold by the company I.S.P.;

(4) copolymers derived from $C_1$–$C_6$ alkyl acrylates or methacrylates and amphiphilic monomers comprising at least one fatty chain;

(5) copolymers derived from hydrophilic acrylates or methacrylates and hydrophobic monomers comprising at least one fatty chain, such as, for example, the polyethylene glycol methacrylate/lauryl methacrylate copolymer;

(6) polymers comprising an aminoplast ether skeleton containing at least one fatty chain, such as the Pure Thix® compounds sold by the company Sud-Chemie; and (7) polyurethane polyethers comprising in their chain both hydrophilic blocks, which may be of a polyoxyethylenated nature, and hydrophobic blocks that may comprise aliphatic blocks alone and/or cycloaliphatic and/or aromatic blocks.

In one embodiment, the polyurethane polyethers comprise at least two hydrocarbon-based lipophilic chains containing from 6 to 30 carbon atoms, separated by a hydrophilic block, the hydrocarbon-based chains possibly being pendent chains or chains at the end of a hydrophilic block. It is possible for one or more pendent chains to be provided. In addition, the polymer may comprise a hydrocarbon-based chain at one or both ends of a hydrophilic block.

The polyurethane polyethers may be multiblock, such as in triblock form. The hydrophobic blocks may be at each end of the chain (for example a triblock copolymer containing a hydrophilic central block) or distributed both at the ends and in the chain (for example a multiblock copolymer). These same polymers may also be graft polymers or starburst polymers.

The fatty-chain nonionic polyurethane polyethers may be triblock copolymers whose hydrophilic block is a polyoxyethylenated chain comprising from 50 to 1000 oxyethylenated groups. The nonionic polyurethane polyethers may comprise a urethane bond between the hydrophilic blocks.

Also included among the fatty-chain nonionic polyurethane polyethers are those whose hydrophilic blocks may be linked to the lipophilic blocks via other chemical bonds.

Non-limiting examples of fatty-chain nonionic polyurethane polyethers that may be used include Ser-Ad FX 1100® from the company Servo Delden, which is a copolymer known under the European and US INCI name "Steareth-100/PEG-136/HMDI Copolymer". Rheolate® 205 containing a urea function, sold by the company Rheox, or alternatively Rheolate® 208, 204 or 212 or Acrysol® RM 184, may also be used. Mention may also be made of the product Elfacos® T210 containing a $C_{12-14}$ alkyl chain and the product Elfacos® T212 containing a $C_{18}$ alkyl chain, from Akzo.

The polyurethane polyethers that may be used include, for example, those described in the article by G. Fonnum, J. Bakke and Fk. Hansen—Colloid Polym. Sci. 271, 380–389 (1993).

In one embodiment, polyurethane polyethers comprising at least one $C_{10}$ to $C_{20}$ fatty chain; and hydroxypropyl guars modified with groups comprising at least one $C_8$ to $C_{22}$ fatty chain, may be used.

Anionic Amphiphilic Polymers Comprising at Least One Fatty Chain

The anionic amphiphilic polymers comprising at least one fatty chain which may be used according to the present invention are chosen from crosslinked and non-crosslinked polymers comprising at least one hydrophilic residue of at least one monomer comprising ethylenic unsaturation bearing a free carboxylic acid function, or a free or partially or totally neutralized sulphonic function, and at least one hydrophobic residue of at least one monomer comprising ethylenic unsaturation bearing a hydrophobic side chain, and optionally at least one crosslinking residue of at least one polyunsaturated monomer.

Synonymously, one skilled in the art can refer to the anionic amphiphilic polymers comprising at least one fatty chain as polymers of at least one hydrophilic unit, at least one hydrophobic unit, and optionally, at least one crosslinking unit.

(A) The at least one monomer comprising ethylenic unsaturation bearing a carboxylic acid function may be chosen from ethacrylic acid, methacrylic acid and acrylic acid, for example, from methacrylic acid and acrylic acid.

The at least one monomer comprising ethylenic unsaturation bearing a hydrophobic side chain can be chosen from (i) fatty alkyl esters of unsaturated carboxylic acids, and (ii) allyl fatty alkyl ethers.

The fatty alkyl esters of unsaturated carboxylic acids may be chosen, for example, from $C_{10-30}$, such as $C_{12-22}$, alkyl ethacrylates, methacrylates, and acrylates. These fatty alkyl esters include, for example, lauryl acrylate, stearyl acrylate, decyl acrylate, isodecyl acrylate and dodecyl acrylate, as well as the corresponding methacrylates, i.e., lauryl methacrylate, stearyl methacrylate, decyl methacrylate, isodecyl methacrylate and dodecyl methacrylate.

The allyl fatty alkyl ethers forming the hydrophobic units of the anionic amphiphilic polymers generally correspond to the formula

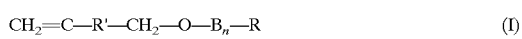

$$CH_2=C-R'-CH_2-O-B_n-R \qquad (I)$$

in which R' may be chosen from hydrogen and $CH_3$, B may be an ethylenoxy group, n may be chosen from 0 or an integer from 1 to 100, R may be a hydrocarbon-based group chosen from alkyl, arylalkyl, aryl, alkylaryl and cycloalkyl radicals comprising from 8 to 30 carbon atoms, such as from 10 to 24 carbon atoms, and for example from 12 to 18 carbon atoms. In one embodiment, R' is hydrogen, n is equal to 10 and R is a stearyl ($C_{18}$) radical.

The monomer from which the at least one cross-linking unit is derived may be chosen from a compound comprising at least two non-conjugated polymerizable double bonds. Examples, which may be mentioned, include diallyl phthalate, allyl (meth)acrylate, divinylbenzene, (poly) ethylene glycol dimethacrylate, methylenebisacrylamide, polyallylsucrose and polyallylpentaerythritol.

Anionic amphiphilic polymers of the type described above are described and prepared, for example, in U.S. Pat. Nos. 3,915,921 and 4,509,949 (copolymers of (meth)acrylic acid and of $C_{10-30}$ alkyl (meth)acrylates), or in European patent EP-0 216 479 B2 (copolymers of (meth)acrylic acid and of allyl fatty alcohol ethers).

In certain embodiments, the polymers used may be chosen from, but are not limited to:

crosslinked polymers of acrylic acid and of $C_{10-30}$ alkyl methacrylate, such as Carbopol® ETD 2020 sold by the company Goodrich;

crosslinked polymers of acrylic acid and of $C_{10-30}$ alkyl acrylate, such as the polymers sold under the names Carbopol® 1382, Pemulen® TR1 and Pemulen® TR2 by the company Goodrich;

methacrylic acid/ethyl acrylate/oxyethylenated stearyl methacrylate (55/35/10) terpolymer;

(meth)acrylic acid/ethyl acrylate/25 EO oxyethylenated behenyl methacrylate terpolymer, and methacrylic acid/ethyl acrylate/steareth-10 allyl ether crosslinked terpolymer.

(B) The amphiphilic polymers comprising, as hydrophilic units, at least one ethylenically unsaturated monomer containing a sulphonic group, in free or partially or totally neutralized form, and at least one hydrophobic portion, are described, for example, in French patent applications 0 016 954 and 0 100 328. Examples of such amphiphilic polymers include:

2-acrylamido-2-methylpropanesulphonic acid (AMPS)/n-dodecylacrylamide copolymer neutralized with sodium hydroxide, the copolymer crosslinked with methylenebisacrylamide comprising 75% by weight of AMPS units neutralized with $NH_3$ and 25% by weight of acrylate units of Genapol® T-250, the copolymer crosslinked with allyl methacrylate comprising 90% by weight of AMPS units neutralized with $NH_3$ and 10% by weight of methacrylate units of Genapol® T-250, or the crosslinked copolymer of allyl methacrylate comprising 80% by weight of AMPS units neutralized with $NH_3$ and 20% by weight of methacrylate units of Genapol® T-250.

In one embodiment of the pulverulent composition according to the present invention, the at least one nonionic and/or anionic amphiphilic polymer comprising at least one fatty chain may be present in an amount ranging from 0.01% to 30% by weight, such as from 0.01% to 15%, relative to the total weight of the composition.

Fatty Acid Sugar Ester

According to the present invention, a fatty acid sugar ester comprises at least one sugar residue and at least one $C_{12}$–$C_{24}$ fatty acid residue.

As used herein, the term "sugar" means a compound containing several alcohol functions, with or without an aldehyde or ketone function, and which comprise at least four carbon atoms. These sugars may be monosaccharides, oligosaccharides or polysaccharides. As used herein, "sugar residue" and "fatty acid residue" refer to the portion of the sugar and fatty acid, respectively, which remains in the ester after reaction between the sugar and fatty acid. Synonymously, one skilled in the art can refer to fatty acid sugar ester as an ester of a sugar and a fatty acid Exemplary sugars that may be used according to the invention include sucrose (or saccharose), glucose, galactose, ribose, fucose, maltose, fructose, mannose, arabinose, xylose and lactose, and derivatives thereof, such alkyl derivatives thereof, for example methyl derivatives such as methylglucose.

The at least one fatty acid sugar ester that may be used according to the invention may be chosen from esters or mixtures of esters of the sugars described above, and of linear and branched, saturated and unsaturated $C_{12}$–$C_{24}$ fatty acids.

The esters may be chosen from mono-, di-, tri- and tetraesters and polyesters, and mixtures thereof.

The esters may be chosen from the oleates, laurates, palmitates, myristates, behenates, cocoates, stearates, linoleates, linolenates, caprates, arachidonates, and mixtures thereof, such as, oleo-palmitate, oleo-stearate, palmito-stearate, and mixed esters.

Exemplary esters include monoesters and diesters, such as mono- and di-oleates, stearates, behenates, oleopalmitates, linoleates, linolenates and oleostearates of sugars chosen from sucrose, glucose, and methylglucose.

Other exemplary esters include the product sold under the name Glucate Do® by the company Amerchol, which is a methylglucose dioleate.

Examples of fatty acid sugar esters or mixtures of esters that may also be mentioned include:

the products sold under the names F160®, F140®, F110®, F90®, F70® and SL40® by the company Crodesta, respectively denoting the sucrose palmitostearates formed from 73% monoester and 27% di- and triester, from 61% monoester and 39% di-, tri- and tetraester, from 52% monoester and 48% di-, tri- and tetraester, from 45% monoester and 55% di-, tri- and tetraester, from 39% monoester and 61% di-, tri- and tetraester, and sucrose monolaurate;

the products sold under the name Ryoto Sugar Esters®, for example bearing the reference B370 and corresponding to the sucrose behenate formed from 20% monoester and 80% di-triester-polyester; and the sucrose mono-di-palmitostearate sold by the company Goldschmidt under the name Tegosoft PSE®.

In the pulverulent composition according to the invention, the at least one fatty acid sugar ester can be present in an amount of less than 10% by weight relative to the total weight of the pulverulent composition, such as less than 5%, for example, ranging from 0.5% to 2% by weight relative to the total weight of the pulverulent composition.

Peroxygenated Salts

Examples of the at least one peroxygenated salt useful in the present invention include, but are not limited to, ammonium and alkali metal persulphates, perborates and percarbonates and also from magnesium peroxide, and mixtures of these compounds.

In one embodiment, persulphates are used, such as sodium and potassium persulphates.

In certain embodiments of the pulverulent composition according to the invention, the at least one peroxygenated salt may be present in an amount by weight ranging from 20% to 70%, such as, for example, from 30% to 60%, relative to the total weight of the composition.

Alkaline Agents

At least one alkaline agent chosen from, for example, urea, alkali metal and alkaline-earth metal silicates, phosphates and carbonates, alkali metal metasilicates, and ammonia precursors such as ammonium salts, may also be present in the pulverulent composition in an amount by weight ranging from 0.01% to 40%, such as from 0.1% to 30% relative to the total weight of the pulverulent composition. According to one embodiment, the at least one alkaline agent may be present in an aqueous composition to be mixed at the time of use with the hydrogen peroxide composition.

Water-soluble Thickening Polymers

In addition, the pulverulent composition according to the invention may also contain at least one water-soluble thickening polymer. These polymers include any water-soluble polymer that is synthetic or of natural origin, conventionally used in the cosmetic field, and may be polymers other than the at least one nonionic and/or anionic amphiphilic polymer comprising at least one fatty chain, as described previously.

Useful synthetic polymers include, but are not limited to, polyvinylpyrrolidone, polyacrylic acid, polyacrylamide, non-crosslinked poly-2-acrylamidopropanesulphonic acid such as, for example, the product sold under the name Simugel EG® by the company SEPPIC, crosslinked poly-2-acrylamido-2-methylpropanesulphonic acid, poly-2-acrylamido-2-methylpropanesulphonic acid crosslinked and partially neutralized with aqueous ammonia, sold under the brand name Hostacerin AMPS® by the company Clariant, mixtures with a synergistic thickening effect of the non-crosslinked poly-2-acrylamido-2-methylpropanesulphonic acid with hydroxylalkylcellulose ethers or with poly(ethylene oxide) as described in U.S. Pat. No. 4,540,510, mixtures with a synergistic thickening effect of a poly(meth)acrylamido($C_1$–$C_4$)alkylsulphonic acid, which may be crosslinked with a crosslinked copolymer of maleic anhydride, and of a ($C_1$–$C_5$)alkyl vinyl ether such as the mixture Hostacerin AMPS®/Stabileze QM® (from the company ISP) and as described in French patent application number 0 014 416.

The thickening polymers of natural origin include, but are not limited to, polymers comprising at least one sugar unit, such as, for example: nonionic guar gums; biopolysaccharide gums of microbial origin such as scleroglucan gum and xanthan gum; gums derived from plant exudates, such as gum arabic, ghatti gum, karaya gum, gum tragacanth, carrageenan, agar and carob gum; pectins; alginates; starches; hydroxy($C_1$–$C_6$)alkylcelluloses and carboxy($C_1$–$C_6$)alkylcelluloses.

For purposes of the present invention, the expression "sugar unit" denotes a portion chosen from monosaccharide portions (i.e., monosaccharides, osides and simple sugars) and oligosaccharide portions (short chains formed from the linking of monosaccharide units, which may be different) or a polysaccharide portion (long chains comprising monosaccharide units, which may be different, i.e., polyholosides and polyosides (homopolyosides and heteropolyosides)). The saccharide units can also be substituted with groups chosen from alkyl, hydroxyalkyl, alkoxy, acyloxy groups, carboxyl groups, and alkyl radicals containing from 1 to 4 carbon atoms.

The nonionic guar gums can be modified or unmodified. The unmodified guar gums may be chosen from, for example, the products sold under the name Guargel® D/15 by the company Goodrich, Vidogum GH 175 by the company Unipectine and under the names Meypro-Guar 50 and Jaguar® C by the company Meyhall.

The modified nonionic guar gums can be modified with $C_1$–$C_6$ hydroxyalkyl groups. The hydroxyalkyl groups include, for example, hydroxymethyl, hydroxyethyl, hydroxypropyl and hydroxybutyl groups. These guar gums are well known in the state of the art and can be prepared, for example, by reacting the corresponding alkene oxides such as, for example, propylene oxides, with the guar gum so as to obtain a guar gum modified with hydroxypropyl groups. In one embodiment, the degree of hydroxyalkylation, which corresponds to the number of alkylene oxide molecules consumed by the number of free hydroxyl functions present on the guar gum can range from 0.4 to 1.2.

Such nonionic guar gums optionally modified with hydroxyalkyl groups are sold, for example, under the trade names Jaguar® HP8, Jaguar® HP60 and Jaguar® HP120, Jaguar® DC 293 and Jaguar® HP 105 by the company Rhone-Poulenc (Meyhall) or under the name Galactasol® 4H4FD2 by the company Aqualon.

The biopolysaccharide gums of microbial origin, such as the scleroglucan and xanthan gums, the gums derived from plant exudates such as gum arabic, ghatti gum, karaya gum, gum tragacanth, carrageenan gum, agar gum and carob gum, the hydroxyalkylcelluloses and carboxymethylcelluloses, pectins, alginates and starches are well known to those skilled in the art and exemplary biopolysaccharide gums are described, for example, in the book by Robert L. Davidson entitled "Handbook of Water Soluble Gums and Resins," published by McGraw Hill Book Company (1980).

Among these gums, the scleroglucans may be represented by the products sold under the name Actigum® CS by the company Sanofi Bio Industries, such as Actigum® CS 11, and under the name Amigel® by the company Alban Muller International. Other scleroglucans, such as the one treated with glyoxal in French patent application No. 2 633 940, can also be used.

The xanthans may be represented by the products sold under the names Keltrol®, Keltrol® T, Keltrof® TF, Keltrol® BT, Keltrol® RD and Keltrol® CG by the company Nutrasweet Kelco, or under the names Rhodicare® S and Rhodicare® H by the company Rhodia Chimie.

Among the starch derivatives that may be mentioned, for example, is the product sold under the name Primogel® by the company Avebe.

The hydroxy($C_1$–$C_6$)alkylcelluloses may, in one embodiment, be hydroxyethylcelluloses, such as those sold under the names Cellosize® QP3L, Cellosize® QP4400H, Cellosize® QP30000H, Cellosize® HEC30000A and Cellosize® Polymer PCG10 by the company Amerchol, or Natrosol® 250HHR, Natrosol® 250 MR, Natrosol® 250M, Natrosol® 250HHXR, Natrosol® 250HHX, Natrosole 250HR and Natrosol® HX by the company Hercules, or Tylose® H1000 by the company Hoechst. The hydroxy ($C_1$–$C_6$)alkylcelluloses may also be hydroxypropylcelluloses such as the products sold under the names Klucel® EF, Klucel® H, Klucel® LHF, Klucel® MF and Klucel® G by the company Aqualon.

The carboxy($C_1$–$C_6$)alkylcelluloses may, in one embodiment, be carboxymethylcellulose, for which mention may be made of the products sold under the names Blanose® 7M8/SF, Blanose® Raffinee 7M, Blanose® 7LF, Blanose® 7MF, Blanose® 9M31F, Blanose® 12M31XP, Blanose® 12M31P, Blanose® 9M31XF, Blanose® 7H, Blanose® 7M31 and Blanose® 7H3SXF by the company Aqualon, or Aquasorb® A500 and Ambergum® 1221 by the company Hercules, or Cellogen® HP810A and Cellogen® HP6HS9 by the company Montello, or Primellose® by the company Avebe.

When the at least one water-soluble thickening polymer is present in the pulverulent compositions of the present invention, it can be present in an amount of less than or equal to 5% by weight relative to the total weight of the composition, such as less than or equal to 3%.

Other Adjuvants

To prevent the pulverulent composition of the invention from being degraded by ambient moisture during storage, it is possible to add thereto at least one moisture absorber such as, for example, silicas, for instance colloidal silica, or fumed silica of hydrophobic or hydrophilic nature. In one embodiment, the at least one moisture absorber may be added in an amount of less than or equal to 3% by weight relative to the total weight of the composition.

The pulverulent composition according to the invention may also contain at least one filler chosen from, for example, clays, binders such as vinylpyrrolidone, lubricants such as polyol stearates, alkali metal stearates, and alkaline-earth metal stearates, and also agents for controlling the evolution of oxygen, such as magnesium carbonate and magnesium oxide, colorants and matt-effect agents such as titanium oxides, and alternatively surfactants chosen from anionic, nonionic and amphoteric surfactants.

The pulverulent composition may also contain at least one polymer chosen from anhydrous cationic and amphoteric conditioning polymers that are well known to those skilled in the art and that are described in French patents Nos. 2 788 974 and 2 788 976, and as described below.

Cationic Polymers

As used herein, the expression "cationic polymer" denotes any polymer containing cationic groups and/or groups which may be ionized into cationic groups.

The cationic polymers may be chosen from any of those already known as improving the cosmetic properties of the hair, such as those described in European patent application EP-A-337 354 and in French patents FR-2 270 846, 2 383 660, 2 598 611, 2 470 596 and 2 519 863.

The cationic polymers may, for example, be chosen from those containing units comprising primary, secondary, tertiary and/or quaternary amine groups, which may either form part of the main polymer chain or may be borne by a side substituent directly attached thereto.

The cationic polymers generally have a number-average molecular mass ranging from 500 to $5 \times 10^6$, such as from $10^3$ to $3 \times 10^6$.

Among the cationic polymers, which may be mentioned, for example, are polyamine, polyaminoamide and polyquaternary ammonium polymers. These polymers are described in French patents Nos. 2 505 348 and 2 542 997. Examples of such polymers include, but are not limited to the following family (1)–(9):

(1) Homopolymers or copolymers derived from acrylic or methacrylic esters or amides and comprising at least one of the units of formula (I), (II), (III) or (IV) below:

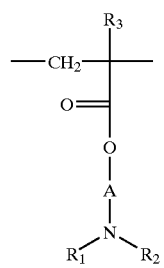

(I)

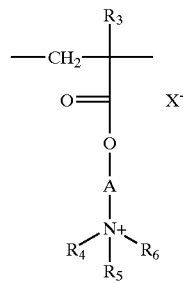

(II)

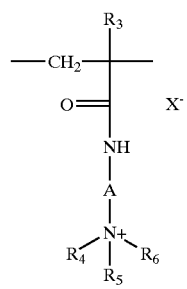

(III)

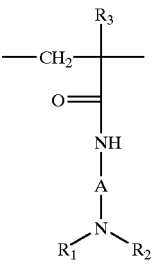

(IV)

in which:
R$_3$, which may be identical or different, may be chosen from hydrogen and a CH$_3$ radical;
A, which may be identical or different, may be chosen from linear and branched alkyl groups of 1 to 6 carbon atoms, such as 2 or 3 carbon atoms, and hydroxyalkyl groups of 1 to 4 carbon atoms;
R$_4$, R$_5$ and R$_6$, which may be identical or different, may be chosen from alkyl groups containing from 1 to 18 carbon atoms and benzyl radicals, such as an alkyl group containing from 1 to 6 carbon atoms;
R$_1$ and R$_2$, which may be identical or different, may be chosen from hydrogen and an alkyl group containing from 1 to 6 carbon atoms, such as methyl or ethyl; and
X$^-$ may be an anion derived from an inorganic or organic acid, such as a methosulphate anion, or an anion chosen from halides such as chloride and bromide.

Copolymers of family (1) can also contain at least one unit derived from comonomers which may be chosen from the family of acrylamides, methacrylamides, diacetone acrylamides, acrylamides and methacrylamides substituted on the nitrogen with lower (C$_1$–C$_4$) alkyls, acrylic acids, methacrylic acids, acrylic esters, methacrylic esters, vinyl-lactams such as vinylpyrrolidone or vinylcaprolactam, and vinyl esters.

Thus, among these polymers of family (1), mention may be made of:
the copolymers of acrylamide and of dimethylaminoethyl methacrylate quaternized with dimethyl sulphate or with a dimethyl halide;
the copolymers of acrylamide and of methacryloyloxy-ethyltrimethylammonium chloride described, for example, in patent application EP-A-080 976;
the copolymers of acrylamide and of methacryloyloxy-ethyltrimethylammonium methosulphate;
quaternized or non-quaternized vinylpyrrolidone/dialkylaminoalkyl acrylate or methacrylate copolymers, as described in detail in French patents 2 077 143 and 2 393 573;
dimethylaminoethyl methacrylate/vinylcaprolactam/vinylpyrrolidone terpolymers;
vinylpyrrolidone/methacrylamidopropyldimethylamine copolymers; and
quaternized vinylpyrrolidone/dimethylaminopropylmethacrylamide copolymers.

(2) The cellulose ether derivatives containing quaternary ammonium groups, described in French patent 1 492 597. These polymers are also defined in the CTFA dictionary as quaternary ammoniums of hydroxyethylcellulose, which has reacted with an epoxide substituted with a trimethylammonium group.

(3) Cationic cellulose derivatives such as cellulose copolymers or cellulose derivatives grafted with a water-soluble monomer of quaternary ammonium, and described, for example, in U.S. Pat. No. 4,131,576, such as hydroxyalkylcelluloses, chosen, for instance from hydroxymethyl-, hydroxyethyl- and hydroxypropylcelluloses grafted, for example, with a salt chosen from methacryloylethyltrimethylammonium, methacrylamidopropyltrimethylammonium and dimethyldiallylammonium salts.

(4) The cationic polysaccharides described, for instance in U.S. Pat. Nos. 3,589,578 and 4,031,307, such as guar gums containing cationic trialkylammonium groups. Guar gums modified with a salt (e.g., chloride) of 2,3-epoxypropyltrimethylammonium may be used, for example.

(5) Polymers comprising piperazinyl units and of divalent alkylene or hydroxyalkylene radicals containing straight or branched chains, optionally interrupted by a heteroatom such as oxygen, sulphur and nitrogen, or by aromatic or heterocyclic rings, as well as the oxidation and/or quaternization products of these polymers. Such polymers are described, for example, in French patents 2 162 025 and 2 280 361;

(6) Water-soluble polyaminoamides prepared, for example, by polycondensation of an acidic compound with a polyamine; these polyaminoamides can be crosslinked with an epihalohydrin, a diepoxide, a dianhydride, an unsaturated dianhydride, a bis-unsaturated derivative, a bis-halohydrin, a bis-azetidinium, a bis-haloacyidiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative. The crosslinking agent can be used in proportions ranging from 0.025 to 0.35 mol per amine group of the polyaminoamide. These polyaminoamides can be alkylated or, if they contain at least one tertiary amine function, they can be quaternized. Such polymers are described, for example, in French patents 2 252 840 and 2 368 508.

(7) The polyaminoamide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical contains from 1 to 4 carbon atoms, such as denotes methyl, ethyl or propyl. Such polymers are described, for example, in French patent 1 583 363.

Among these derivatives, mention may be made, for example, of the adipic acid/dimethylaminohydroxypropyl/diethylenetriamine polymers.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid may range, for example, from 0.8:1 to 1.4:1; the polyaminoamide resulting therefrom may be reacted with epichlorohydrin in a molar ratio of epichlorohydrin relative to the secondary amine group of the polyaminoamide ranging from 0.5:1 to 1.8:1. Such polymers are described, for example, in U.S. Pat. Nos. 3,227,615 and 2,961,347.

(9) Cyclopolymers of alkyldiallylamine or of dialkyldiallylammonium, such as the homopolymers or copolymers containing, as main constituent of the chain, at least one unit corresponding to formula (V) or (VI):

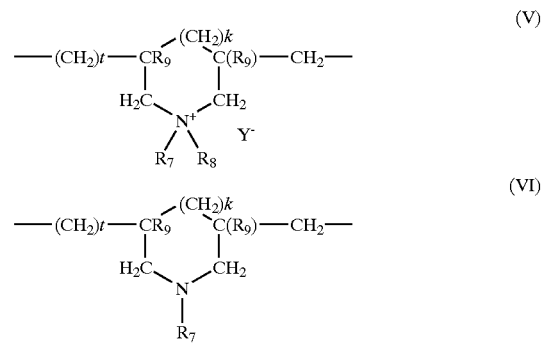

wherein k and t may be equal to 0 or 1, the sum k+t being equal to 1;

$R_9$ may be chosen from hydrogen and a methyl radical;

$R_7$ and $R_8$, which may be identical or different, may be chosen from an alkyl group having from 1 to 8 carbon atoms, a hydroxyalkyl group in which the alkyl group may, in one embodiment, have 1 to 5 carbon atoms, and a lower $C_1$–$C_4$ amidoalkyl group, or $R_7$ and $R_8$ can denote, together with the nitrogen to which they are attached, heterocyclic groups such as piperidyl or morpholinyl; in one embodiment, $R_7$ and $R_8$, independently of each other, may be chosen from alkyl groups having from 1 to 4 carbon atoms; $Y^-$ may be an anion such as bromide, chloride, acetate, borate, citrate, tartrate, bisulphate, bisulphite, sulphate, and phosphate. These polymers are described, for example, in French patent 2 080 759 and in its Certificate of Addition 2 190 406.

(10) The quaternary diammonium polymer containing repeating units corresponding to the formula (VII):

in which:

$R_{10}$, $R_{11}$, $R_{12}$ and $R_{13}$, which may be identical or different, may be chosen from aliphatic, alicyclic and arylaliphatic radicals containing from 1 to 20 carbon atoms and from lower hydroxyalkylaliphatic radicals, or alternatively $R_{10}$, $R_{11}$, $R_{12}$ and $R_{13}$, together or separately, may constitute, with the nitrogen to which they are attached, heterocycles optionally comprising a second heteroatom other than nitrogen, or alternatively $R_{10}$, $R_{11}$, $R_{12}$ and $R_{13}$ may be chosen from linear and branched $C_1$–$C_6$ alkyl radicals substituted with groups chosen from nitrile, ester, acyl and amide groups, and a group —CO—O—$R_{14}$—D or —CO—NH—$R_{14}$—D where $R_{14}$ may be an alkylene and D may be a quaternary ammonium group;

$A_1$ and $B_1$, which may be identical or different, may be chosen from linear and branched, saturated and unsaturated polymethylene groups containing from 2 to 20 carbon atoms, and which may contain, linked to or intercalated in the main chain, at least one entity chosen from aromatic rings, oxygen, sulphur, sulphoxide, sulphone, disulphide, amino, alkylamino, hydroxyl, quaternary ammonium, ureido, amide, and ester, and $X^-$ may be an anion derived from an inorganic or organic acid;

$A_1$, $R_{10}$ and $R_{12}$ can form, with the two nitrogens to which they are attached, a piperazine ring. In addition, if $A_1$ is a radical chosen from linear and branched, saturated and unsaturated alkylene and hydroxyalkylene radicals, $B_1$ can also denote a group —$(CH_2)_{n'}$—CO—D—OC—$(CH_2)_{n'}$— in which n' may range from 1 to 100, such as from 1 to 50, and D may be chosen from:

a) a glycol residue of formula: —O—Z—O—, where Z may be chosen from linear and branched hydrocarbon-based radicals and a group corresponding to one of the following formulae:

—$(CH_2$—$CH_2$—O$)_x$—$CH_2$—$CH_2$—

—[$CH_2$—$CH(CH_3)$—O$]_y$—$CH_2$—$CH(CH_3)$— where x and y may each be an integer ranging from 1 to 4, representing a defined and unique degree of polymerization or any number ranging from 1 to 4 representing an average degree of polymerization;

b) a bis-secondary diamine residue such as a piperazine derivative;

c) a bis-primary diamine residue of formula: —NH—Y—NH—, where Y may be chosen from linear and branched hydrocarbon-based radicals, or alternatively the divalent radical —$CH_2$—$CH_2$—S—S—$CH_2$—$CH_2$—; or d) a ureylene group of formula: —NH—CO—NH—.

In one embodiment, $X^-$ is an anion such as chloride and bromide.

These polymers may have a number-average molecular mass ranging from 1000 to 100,000.

Polymers of this family are described, for example, in French patent Nos. 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Other exemplary polymers of family (10) can comprise repeating units corresponding to the following formula (VIII):

$$\begin{array}{cc} R_{10} & R_{12} \\ | & | \\ -N^+-(CH_2)_{n''}-N^+-(CH_2)_{p}- \\ | & | \\ R_{11} \ X^- & R_{13} \ X^- \end{array} \quad (VIII)$$

in which $R_{10}$, $R_{11}$, $R_{12}$ and $R_{13}$, which may be identical or different, may be chosen from alkyl and hydroxyalkyl radicals containing from 1 to 4 carbon atoms, n" and p may be integers ranging from 2 to 20, and $X^-$ may be an anion derived from an inorganic or organic acid.

(11) Polyquaternary ammonium polymers comprising repeating units of formula (IX):

$$\left[ \begin{array}{cc} CH_3 \ \ X & X \ \ CH_3 \\ | & | \\ -N^+-(CH_2)_{p'}-NH-CO-D-NH-(CH_2)_{p'}-N^+-(CH_2)_2-O-(CH_2)_2- \\ | & | \\ CH_3 & CH_3 \end{array} \right] \quad (IX)$$

in which p' may be an integer ranging from 1 to 6, D may be a bond or may be a group —$(CH_2)_r$—CO— in which r may be a number equal to 4 or 7, $X^-$ may be an anion;

Such polymers may be prepared according to the processes described in, for example, U.S. Pat. Nos. 4,157,388, 4,702,906 and 4,719,282, and European patent application EP-A-122 324.

(12) Quaternary polymers of vinylpyrrolidone and of vinylimidazole.

(13) Polyamines such as the product that is referenced to under the name "Polyethylene glycol (15) Tallow polyamine" in the CTFA dictionary.

(14) Crosslinked methacryloyloxy($C_1$–$C_4$)alkyltri($C_1$–$C_4$)alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, such as methylenebisacrylamide. A crosslinked acrylamide/methacryloyloxyethyltrimethylammonium chloride copolymer (20/80 by weight) in the form of a dispersion containing 50% by weight of the copolymer in mineral oil can be used, in one embodiment. This dispersion is sold under the name "Salcare® SC 92" by the company Allied Colloids. A crosslinked methacryloyloxyethyltrimethylammonium chloride homopolymer containing 50% by weight of the homopolymer in mineral oil or in a liquid ester can also be used. These dispersions are sold under the names "Salcare® SC 95" and "Salcare® SC 96" by the company Allied Colloids.

Other cationic polymers, which can be used, include polyalkyleneimines, such as polyethyleneimines, polymers containing vinylpyridine or vinylpyridinium units, condensates of polyamines and of epichlorohydrin, quaternary polyureylenes and chitin derivatives.

Amphoteric Polymers

The amphoteric polymers useful in the present invention may be chosen from polymers comprising units K and M randomly distributed in the polymer chain, in which K is a unit derived from a monomer comprising at least one basic nitrogen atom and M is a unit derived from an acidic monomer comprising at least one carboxylic or sulphonic group, or alternatively K and M may be chosen from groups derived from zwitterionic carboxybetaine or sulphobetaine monomers;

K and M may also be chosen from a cationic polymer chain comprising a group chosen from at least one primary, secondary, tertiary and quaternary amine group, in which at least one of the amine groups bears a carboxylic or sulphonic group linked via a hydrocarbon-based radical, or alternatively K and M form part of a chain of a polymer containing an α,β-dicarboxylic ethylene unit in which one of the carboxylic groups has been made to react with a polyamine comprising at least one amine chosen from primary and secondary amine groups.

The amphoteric polymers corresponding to the above definition can be chosen from the following polymers.

(1) Polymers resulting from the copolymerization of at least one monomer derived from a vinyl compound bearing a carboxylic group, such as acrylic acid, methacrylic acid, maleic acid, α-chloroacrylic acid, and at least one basic monomer derived from a substituted vinyl compound containing at least one basic atom, such as dialkylaminoalkyl methacrylate and acrylate, dialkylaminoalkylmethacrylamide and -acrylamide. Such compounds are described, for example, in U.S. Pat. No. 3,836,537. Mention may also be made of the sodium acrylate/acrylamidopropyltrimethylammonium chloride copolymer.

The vinyl compound may also be a dialkyldiallylammonium salt such as dimethyldiallylammonium chloride.

(2) Polymers containing units derived from:

a) at least one monomer chosen from acrylamides and methacrylamides substituted on the nitrogen with an alkyl radical, b) at least one acidic comonomer containing at least one reactive carboxylic group, and c) at least one basic comonomer such as esters containing substituents chosen from primary, secondary, tertiary and quaternary amine substituents of acrylic and methacrylic acids and the product of quaternization of dimethylaminoethyl methacrylate with dimethyl or diethyl sulphate.

In one embodiment, the N-substituted acrylamides or methacrylamides which can be used include groups in which the alkyl radicals contain from 2 to 12 carbon atoms, such as N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers may be chosen, for example, from acrylic acid, methacrylic acid, crotonic acid, itaconic acid, maleic acid and fumaric acid and alkyl monoesters, having 1 to 4 carbon atoms, of maleic or fumaric acids or anhydrides.

The basic comonomers may be chosen, for example, from aminoethyl, butylaminoethyl, N,N'-dimethylaminoethyl and N-tert-butylaminoethyl methacrylates.

(3) Crosslinked and alkylated polyaminoamides partially or totally derived from polyaminoamides of formula:

in which $R_{19}$ may be chosen from a divalent radical derived from a saturated dicarboxylic acid, a mono- or dicarboxylic aliphatic acid containing an ethylenic double bond, an ester of a lower alkanol, having from 1 to 6 carbon atoms, of these acids, and a radical derived from the addition of any one of the acids to amines chosen from bis(primary) and bis(secondary) amines, and Z may be chosen from a bis(primary), mono- and bis(secondary) polyalkylene-polyamine radicals, such as:

a) in proportions of from 60 to 100 mol %, the radical

where x'=2 and p=2 or 3, or alternatively x=3 and p=2, this radical being derived from amines chosen from diethylenetriamine, triethylenetetraamine, and dipropylenetriamine;

b) in proportions of from 0 to 40 mol %, the radical (XI) above in which x'=2 and p''=1 and which can be derived from groups chosen from ethylenediamine and piperazine:

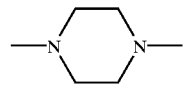

c) in proportions of from 0 to 20 mol %, the —NH—$(CH_2)_6$—NH— radical, which can be derived from hexamethylenediamine, these polyaminoamines can be crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyaminoamide and alkylated by the action of acrylic acid, chloroacetic acid or an alkane sultone, or salts thereof.

In one embodiment, the saturated carboxylic acids are chosen from acids having 6 to 10 carbon atoms, such as adipic acid, 2,2,4-trimethyladipic acid and 2,4,4-trimethyladipic acid, terephthalic acid and acids containing an ethylenic double bond such as, for example, acrylic acid, methacrylic acid and itaconic acid.

The alkane sultones used in the alkylation may be chosen from propane sultone and butane sultone, and the salts of the alkylating agents may be chosen from sodium and potassium salts.

(4) Polymers containing zwitterionic units of formula:

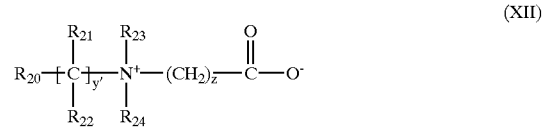

in which $R_{20}$ may be chosen from a polymerizable unsaturated group such as an acrylate, methacrylate, acrylamide or methacrylamide group; y' and z may be chosen from an integer ranging from 1 to 3;

$R_{21}$ and $R_{22}$, which may be identical or different, may be chosen from hydrogen, methyl, ethyl and propyl;

$R_{23}$ and $R_{24}$, which may be identical or different, may be chosen from hydrogen and an alkyl radical such that the sum of the carbon atoms in $R_{23}$ and $R_{24}$ does not exceed 10.

The polymers comprising such units can also contain units derived from non-zwitterionic monomers such as monomers chosen from dimethyl and diethylaminoethyl acrylates and methacrylates, alkyl acrylates, alkyl methacrylates, acrylamides, methacrylamides, and vinyl acetate.

By way of example, mention may be made of the copolymer of butyl methacrylate/dimethyl carboxymethylammonio ethyl methacrylate such as the product sold under the name Diaformer Z301® by the company Sandoz.

(5) Polymers derived from chitosan containing monomer units corresponding to formulae (XIII), (XIV) and (XV) below:

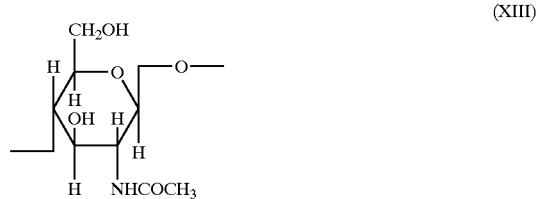

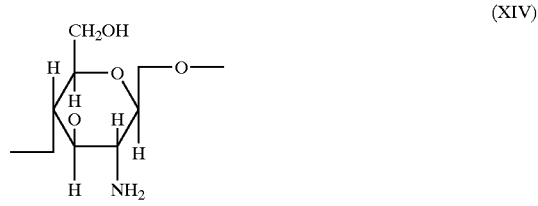

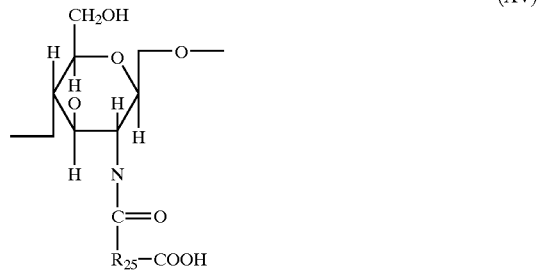

the unit (XIII) being present in proportions ranging from 0 to 30%, the unit (XIV) in proportions ranging from 5 to 50% and the unit (XV) in proportions ranging from 30 to 90%, where in unit (XV), $R_{25}$ may be a radical of the formula:

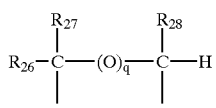

in which q is 0 or 1;

if q=0, then $R_{26}$, $R_{27}$ and $R_{28}$, which may be identical or different, are each chosen from hydrogen, methyl, hydroxyl, acetoxy and amino residues, monoalkylamine residues, and dialkylamine residues, which are optionally interrupted by at least one nitrogen atom and/or optionally substituted with at least one group chosen from amine, hydroxyl, carboxyl, alkylthio, and sulphonic groups, and an alkylthio residue in which the alkyl group bears an amino residue, at least one of the radicals $R_{26}$, $R_{27}$ and $R_{28}$ being, in this case, hydrogen;

or, if q=1, $R_{26}$, $R_{27}$ and $R_{28}$ each are hydrogen, as well as the salts formed by these compounds with bases or acids.

6) Polymers derived from the N-carboxyalkylation of chitosan, such as N-carboxymethylchitosan and N-carboxybutylchitosan.

7) Polymers corresponding to the general formula (XVI) as described, for example, in French patent 1 400 366:

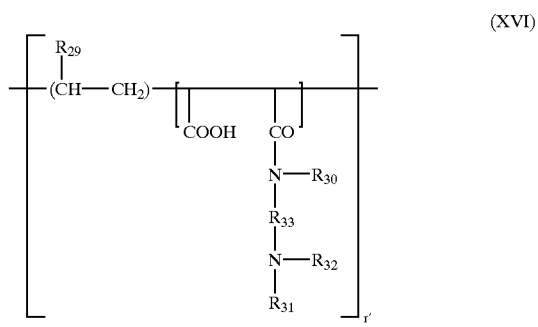

(XVI)

in which $R_{29}$ may be chosen from hydrogen, a $CH_3O$ radical, a $CH_3CH_2O$ radical, and a phenyl radical, $R_{30}$ may be chosen from hydrogen and a lower alkyl radical such as methyl and ethyl, $R_{31}$ may be chosen from hydrogen and a lower alkyl radical such as methyl and ethyl, $R_{32}$ may be chosen from a lower alkyl radical such as methyl and ethyl, and a radical corresponding to the formula: $-R_{33}-N(R_{31})_2$, $R_{33}$ may be chosen from $-CH_2-CH_2-$, $-CH_2-CH_2-CH_2-$ and $-CH_2-CH(CH_3)-$ groups, $R_{31}$ may be chosen from hydrogen and a $C_1-C_6$ alkyl radical, r' may be chosen such that the molecular weight ranges from 500 to 6,000,000, such as, for example, from 1,000 to 1,000,000.

8) Amphoteric polymers of the type $-D-X-D-X-$ chosen from:

a) polymers obtained by the action of chloroacetic acid or sodium chloroacetate on compounds containing at least one unit of formula:

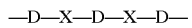 (XVII)

where D may be a radical

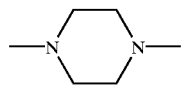

and X may be the symbol E or E',

E or E', which may be identical or different, may be chosen from divalent alkylene radicals comprising at least one chain chosen from straight and branched chains comprising up to 7 carbon atoms in the main chain, wherein said divalent alkylene radicals are optionally substituted with at least one hydroxyl group;

E or E' can additionally comprise groups chosen from: at least one heteroatom chosen from oxygen, nitrogen and sulphur atoms; and 1 to 3 rings chosen from aromatic and heterocyclic rings. The oxygen, nitrogen and sulphur atoms can be present in the form of at least one group chosen from ether, thioether, sulphoxide, sulphone, sulphonium, alkylamine, alkenylamine, hydroxyl, benzylamine, amine oxide, quaternary ammonium, amide, imide, alcohol, ester, and urethane groups;

b) polymers of formula:

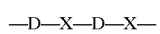 (XVIII)

where D may be a radical

and X may be the symbol E or E' and at least once E'; E having the meaning given above and E' being chosen from divalent alkylene radicals comprising at least one chain chosen from straight and branched chains comprising up to 7 carbon atoms in the main chain, wherein said divalent alkylene radicals are optionally substituted with at least one hydroxyl group. E' can also comprise at least one nitrogen atom substituted with an alkyl chain which can be interrupted by an oxygen atom, wherein said alkyl chain comprises at least one functional group chosen from at least one carboxyl function and hydroxyl functional groups, and wherein said at least one alkyl chain is betainized by reaction with a reactant chosen from chloroacetic acid and sodium chloroacetate.

(9) $(C_1-C_5)$alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also contain other vinyl comonomers such as vinylcaprolactam.

In some embodiments, the following cationic or amphoteric polymers may be used:

(i) among the cationic polymers:

the dimethyldiallylammonium chloride homopolymer sold under the name Merquat® 100DRY by the company Merck;

the copolymers of dimethyldiallylammonium chloride and of acrylamide that are sold under the name Merquat® 2200 by the company Calgon;

the polymers of poly(quaternary ammonium) type prepared and described in French patent 2 270 846, comprise repeating units of formulae (W) and (U) below:

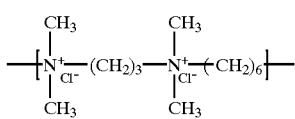

(W)

such as those whose weight-average molar mass, determined by gel permeation chromatography, may range from 9500 to 9900;

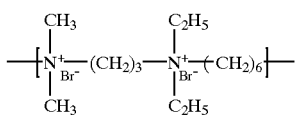

(U)

such as those whose weight-average molar mass, determined by gel permeation chromatography, may be 1200;

polymers of poly(quaternary ammonium) type of family (11) and of formula (IX) in which $X^-$ may be chlorine, such as those whose weight-average molecular mass may be less than 100 000, for example less than or equal to 50 000; and (ii) among the amphoteric polymers:

the dimethyldiallylammonium chloride/acrylic acid (80/20) copolymer sold under the name Merquat® 280 Dry by the company Calgon (CTFA name: Polyquaternium 22);

the dimethyldiallylammonium chloride/acrylic acid (95/5) copolymer sold under the name Merquat® 295 Dry by the company Calgon (CTFA name: Polyquaternium 22);

the copolymer of methacrylamidopropyltrimonium chloride, of acrylic acid and of ethyl acrylate, sold under the name Merquat® 2001 by the company Calgon (CTFA name: Polyquaternium 47); and the acrylamide/dimethyldiallylammonium chloride/acrylic acid terpolymer sold under the name Merquat® Plus 3330 Dry by the company Calgon (CTFA name: Polyquaternium 39).

When they are present in the inventive pulverulent compositions, the cationic and/or amphoteric polymers may be present in an amount by weight of less than or equal to 20% relative to the total weight of the said composition, such as less than or equal to 8%.

Preparation of the Pulverulent Composition According to the Invention

The pulverulent composition can prepared by simple addition of the desired amount of the at least one fatty acid sugar ester, described above, to a powdery mixture comprising at least one peroxygenated salt, at least one amphiphilic polymer chosen from anionic and nonionic amphiphilic polymers, and optionally at least one alkaline agent, at least one water-soluble thickening polymer and/or at least one moisture absorber, and silica.

Aqueous Hydrogen Peroxide Composition

In one embodiment, the aqueous hydrogen peroxide composition of the invention does not have a titre of more than 40 volumes, and its titre may range from 2 to 40 volumes.

The composition may be formulated for cosmetic use and may contain at least one ingredient chosen from the following:

(i) at least one surfactant chosen from anionic and nonionic surfactants and optionally at least another surfactant chosen from nonionic, anionic, cationic, and zwitterionic surfactants, the at least one surfactant may be present in a total amount by weight ranging from 0.1% to 10%, such as from 0.1% to 5% relative to the total weight of the aqueous hydrogen peroxide composition;

(ii) a combination of at least two nonionic surfactants with HLB (Hydrophilic Lipophilic Balance) values that are different, and at least one of which is less than or equal to 5 according to the Griffin scale, in an amount by weight ranging from 1.5% to 40%, for example from 1.5% to 20% relative to the total weight of the aqueous hydrogen peroxide composition; (Griffin defined in the publication J. Soc. Cosm. Chem. 1954 (Volume 5), pages 249–256, or the HLB value determined experimentally and as described in the book by F. Puisieux and M. Seiller, entitled "Galenica 5: Dispersed systems—Volume 1—Surface agents and emulsions—Chapter IV—Notions of HLB and of critical HLB, pages 153–194—paragraph 1.1.2. Determination of HLB experimentally, pages 164–180);

(iii) a combination of a nonionic surfactant with an HLB (Hydrophilic Lipophilic Balance) value of less than or equal to 5 according to the Griffin scale and an anionic surfactant, in a total amount by weight ranging from 1% to 30%, such as from 1.5% to 15%, relative to the total weight of the aqueous hydrogen peroxide composition; and (iv) at least one thickening polymer irrespective of its chemical nature, in an amount by weight ranging from 0.1% to 10%, such as from 0.1% to 5%, relative to the total weight of the aqueous hydrogen peroxide composition;

the at least one thickening polymer optionally being combined with a surfactant of any type in a weight proportion ranging from 0.1% to 10%, for example from 0.1% to 5% relative to the total weight of the aqueous hydrogen peroxide composition.

This at least one thickening polymer may be chosen, for example, from the water-soluble thickening polymers already described above, amphiphilic polymers comprising at least one fatty chain and which may be chosen from nonionic and anionic polymers such as those described above for the non-volatile pulverulent composition, or alternatively from cationic and amphoteric polymers such as those described below.

Because the hydrogen peroxide composition is aqueous, the nonionic and anionic amphiphilic polymers may also be in a form chosen from water-based solutions and dispersions.

Exemplary polymers include fatty-chain nonionic polyurethane polyethers such as:

Aculyn® 44 and Aculyn® 46 from the company Rohm & Haas [Aculyn® 46 is a polycondensate of polyethylene glycol containing 150 or 180 mol of ethylene oxide, of stearyl alcohol and of methylenebis(4-cyclohexyl isocyanate) (SMDI), at a concentration of 15% by weight in a matrix of maltodextrin (4%) and water (81%); Aculyn® 44 is a polycondensate of polyethylene glycol containing 150 or 180 mol of ethylene oxide, of decyl alcohol and of methylenebis(4-cyclohexyl isocyanate) (SMDI), at a concentration of 35% by weight in a mixture of propylene glycol (39%) and water (26%)];

the product DW 1206B® from Rohm & Haas, containing a $C_{20}$ alkyl chain and a urethane bond, sold at a solids content of 20% in water; and the products Rheolate® 255, Rheolate® 278 and Rheolate® 244 sold by the company Rheox, or the products DW 1206F® and DW 1206J® sold by the company Rohm & Haas.

Other exemplary polymers include fatty-chain anionic amphiphilic polymers such as, for example:

crosslinked terpolymers of methacrylic acid, and of ethyl acrylate, of polyethylene glycol (10 EO) stearyl ether (Steareth 10), sold by the company Allied Colloids under the names Salcare® SC 80 and Salcare® SC 90 which are aqueous 30% emulsions of a crosslinked terpolymer of methacrylic acid, of ethyl acrylate and of steareth-10 allyl ether (40/50/10); and the methacrylic acid/methyl acrylate/ethoxylated (40 EO) behenyl dimethyl-meta-isopropenylbenzylisocyanate as an aqueous 25% dispersion, described in Example 3 of patent EP-A-0 173 109.

Among the amphiphilic polymers comprising at least one fatty chain and of amphoteric type, mention may be made of those described and prepared in patent application WO 98/44012, and acrylic acid/(meth)acrylamidopropyltrimethylammonium chloride/stearyl methacrylate copolymers.

Among the amphiphilic polymers comprising at least one fatty chain and of cationic type, mention may be made, for example, of the following polymers.

(I)—Amphiphilic polymers chosen from quaternized cellulose derivatives including, for example;

quaternized celluloses modified with groups comprising at least one fatty chain, such as alkyl, arylalkyl or alkylaryl groups comprising at least 8 carbon atoms, or mixtures thereof; and quaternized hydroxyethylcelluloses modified with groups comprising at least one fatty chain, such as alkyl, arylalkyl or alkylaryl groups comprising at least 8 carbon atoms, or mixtures thereof.

The alkyl radicals borne by the above quaternized celluloses or hydroxyethylcelluloses may comprise from 8 to 30 carbon atoms. In one embodiment, the aryl radicals may denote groups chosen from phenyl, benzyl, naphthyl and anthryl groups.

Examples of quaternized alkylhydroxyethylcelluloses containing $C_8$–$C_{30}$ fatty chains which may be mentioned are the products Quatrisoft® LM 200, Quatrisoft® LM-X 529-18-A, Quatrisoft® LM-X 529-18B ($C_{12}$ alkyl) and Quatrisoft® LM-X 529-8 ($C_{18}$ alkyl) sold by the compa Amerchol and the products Crodacel® QM, Crodacel® QL ($C_{12}$ alkyl) and Crodacel® QS ($C_{18}$ alkyl) sold by the company Croda.

(II)—Amphiphilic polymers chosen from quaternized and non-quaternized polyacrylates containing non-cyclic amino side groups, which have, for example, hydrophobic groups of the type such as steareth 20 (polyoxyethylenated (20) stearyl alcohol).

As examples of polyacrylates containing amino side chains, mention may be made of the polymers 8781-121 B or 9492-103 sold by the company National Starch.

(III)—Amphiphilic polymers chosen from the family of cationic associative polyurethanes described by the Applicant in French patent application number 0 009 609; they may be represented by the general (XIX) below:

R—X—(P)$_{n'''}$-L-(Y)$_m$-L'-(P')$_{p'''}$-X'—R'  (XIX)

in which:

R and R', which may be identical or different, may be chosen from hydrophobic groups and hydrogen;

X and X', which may be identical or different, may be chosen from groups comprising a tertiary or quaternary amine optionally comprising a hydrophobic group, or alternatively, L";

L, L' and L", which may be identical or different, may be chosen from groups derived from diisocyanate;

P and P', which may be identical or different, may be chosen from groups comprising a tertiary or quaternary amine optionally comprising a hydrophobic group;

Y may be chosen from hydrophilic groups; and n''', m and p''' each, independently of each other, may range from 0 to 1000;

the molecule containing at least one group chosen from tertiary and quaternary amines, and at least one hydrophobic group.

Another useful family of cationic associative polyurethanes is the one corresponding to formula (XIX) above in which:

R and R' both independently may be a hydrophobic group,

X and X' both independently may be L", n''' and p''' may range from 1 to 1000, and L, L', and L", which may be identical or different, may be chosen from groups derived from diisocyanate, P and P', which may be identical or different, may be chosen from groups comprising a tertiary or quaternary amine optionally comprising a hydrophobic group, Y may be chosen from hydrophilic groups, and m may range from 0 to 1000.

Another family of cationic associative polyurethanes is the one corresponding to formula (XIX) above in which:

R and R' both independently may be a hydrophobic group,

X and X' both independently may be a quaternary amine, n''' and p''' are 0, and

L and L', which may be identical or different, may be chosen from groups derived from diisocyanate, Y may be chosen from hydrophilic groups, and m may range from 0 to 1000.

The weight-average molecular mass of the cationic associative polyurethanes may range from 400 to 10 000, for example, from 1000 to 5000.

The term "hydrophobic group" means a radical or polymer containing a saturated or unsaturated, linear or branched hydrocarbon-based chain which may contain at least one hetero atom such as P, O, N and S, or a radical containing a perfluoro or silicone chain. When "hydrophobic group" denotes a hydrocarbon-based radical, the hydrophobic group comprises at least 10 carbon atoms The hydrocarbon-based group can be derived from a monofunctional compound.

By way of example, the hydrophobic group may be derived from a fatty alcohol such as stearyl alcohol, dodecyl alcohol or decyl alcohol. It may also denote a hydrocarbon-based polymer such as, for example, polybutadiene.

When X and/or X' are groups comprising a tertiary or quaternary amine, X and/or X' may represent one of the following formulae:

$$-\!\!-\!\!N\!-\!\!R_2\!-\!\!-\quad \text{or} \quad -\!\!-\!\!\overset{R_3}{\underset{R_1}{\overset{|}{N_+}}}\!-\!\!R_2\!-\!\!-\quad \text{for X}$$
$$\underset{R_1}{|}\qquad\qquad\qquad\quad A^-$$

$$-\!\!-\!\!R_2\!-\!\!N\!-\!\!-\quad \text{or} \quad -\!\!-\!\!R_2\!-\!\!\overset{R_3}{\underset{R_1}{\overset{|}{N_+}}}\!-\!\!-\quad \text{for X'}$$
$$\underset{R_1}{|}\qquad\qquad\qquad\quad A^-$$

in which:

$R_2$ may be chosen from linear and branched alkylene radicals containing from 1 to 20 carbon atoms optionally comprising at least one ring chosen from saturated and unsaturated rings, an arylene radical, wherein at least one of the carbon atoms can be replaced with a heteroatom chosen from N, S, O and P;

$R_1$ and $R_3$, which may be identical or different, may be chosen from linear and branched $C_1$–$C_{30}$ alkyl and linear and branched $C_1$–$C_{30}$ alkenyl radicals and an aryl radical, at least. one of the carbon atoms possibly being replaced with a hetero atom chosen from N, S, O and P; and $A^-$ may be a physiologically acceptable counterion.

The groups L, L' and L" may represent a group of formula:

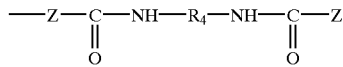

in which:

Z may be chosen from —O—, —S— and —NH—; and $R_4$ may be chosen from linear and branched alkylene radicals containing from 1 to 20 carbon atoms, optionally comprising a saturated or unsaturated ring or an arylene radical, at least one of the carbon atoms possibly being replaced with a hetero atom chosen from N, S, O and P.

The groups P and P' comprising a tertiary or quaternary amine may be chosen from at least one of the following formulae:

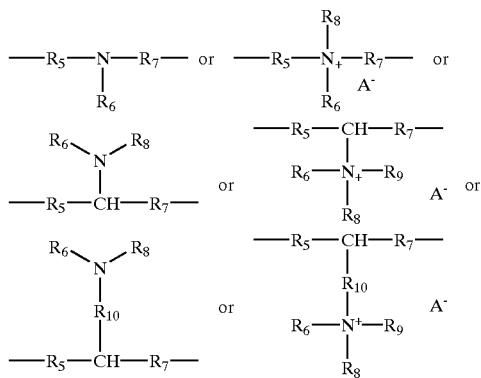

in which:

$R_5$ and $R_7$, which may be identical or different, may be chosen from linear and branched alkylene radicals containing from 1 to 20 carbon atoms optionally comprising at least one ring chosen from saturated and unsaturated rings, an arylene radical, wherein at least one of the carbon atoms can be replaced with a heteroatom chosen from N, S, O and P;

$R_6$, $R_8$ and $R_9$, which may be identical or different, may be chosen from linear and branched $C_1$–$C_{30}$ alkyl and linear and branched $C_1$–$C_{30}$ alkenyl radicals and an aryl radical, at least one of the carbon atoms possibly being replaced with a hetero atom chosen from N, S, O and P;

$R_{10}$ may be chosen from a linear and branched, optionally unsaturated alkylene groups which may contain at least one hetero atom chosen from N, O, S and P, and $A^-$ may be a physiologically acceptable counterion.

With respect to the definition of Y, the term "hydrophilic group" means a polymeric or non-polymeric water-soluble group.

By way of example, when the hydrophilic group is non-polymeric, exemplary polymers include diethylene glycol and hexaethylene glycol.

When, in accordance with an embodiment of the invention, the hydrophilic group comprises hydrophilic polymers, exemplary polymers include polyethers, sulphonated polyesters, sulphonated polyamides or a mixture of these polymers. The hydrophilic compound can be a polyether, such as a poly(ethylene oxide) or poly(propylene oxide).

The cationic associative polyurethane of formula (XIX) according to the invention can be formed from various compounds, each containing at least one labile hydrogen. These various groups can be successively reacted together so as to form the various blocks of the polymer.

A first type of compound involved in the preparation of the polymer of formula (XIX) of the invention may be a compound comprising at least one amine chosen from tertiary and quaternary amines. This compound may be multifunctional. If the compound is difunctional, i.e., the compound can comprise two labile hydrogen atoms borne, for example, by a hydroxyl, secondary amine, tertiary amine or thiol function. A mixture of multifunctional and difunctional compounds in which the percentage of multifunctional compounds is low may also be used.

As mentioned above, this compound may comprise more than one tertiary or quaternary amine. The compound can be a polymer having a repeat unit including those chosen from tertiary and quaternary amines. Compounds of this type may be represented by one of the following formulae:

or

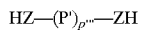

in which Z may be chosen from —O—, —S— and —NH—, n''' and p''' are 0, and P and P', which may be identical or different, may be chosen from groups comprising a tertiary or quaternary amine optionally comprising a hydrophobic group, such as any of the groups described above.

Exemplary compounds include N-methyldiethanolamine, N-tert-butyldiethanolamine and N-sulphoethyldiethanolamine.

In one embodiment, a second compound involved in the preparation of the polymer of formula (XIX) may be a diisocyanate corresponding to the formula:

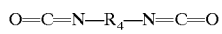

in which $R_4$ may be chosen from linear and branched alkylene radicals containing from 1 to 20 carbon atoms, optionally comprising a saturated or unsaturated ring or an arylene radical, at least one of the carbon atoms possibly being replaced with a hetero atom chosen from N, S, O and P.

By way of example, mention may be made of methylenediphenyl diisocyanate, methylenecyclohexane diisocyanate, isophorone diisocyanate, toluene diisocyanate, naphthalene diisocyanate, butane diisocyanate and hexane diisocyanate.

A third compound involved in the preparation of the polymer of formula (XIX) may be a hydrophobic compound intended to form the terminal hydrophobic block of the polymer of formula (XIX).

This hydrophobic block may be formed from a compound comprising a labile hydrogen borne, for example, by a hydroxyl, primary or secondary amine, or thiol function. The compound may be a monofunctional compound. The functional portion of this compound may contain a tertiary or quaternary amine. The hydrophobic portion of this compound may or may not be a polymer.

By way of example, this compound may be a fatty alcohol such as stearyl alcohol, dodecyl alcohol or decyl alcohol. When this compound comprises a polymeric chain, it may be, for example, α-hydroxylated hydrogenated polybutadiene.

The hydrophobic block of the compound of formula (XIX) may also result from the quaternization reaction of the tertiary amine of the compound comprising at least one tertiary amine unit. Thus, the hydrophobic group can be introduced via the quaternizing agent. The quaternizing agent can be a compound of the type RQ or R'Q, in which R and R' both independently are a hydrophobic group, and Q is chosen from halides and sulphates.

The cationic associative polyurethane of the invention may also comprise a hydrophilic block. This block may be provided by a fourth type of compound involved in the preparation of the polymer. This compound may be multifunctional or difunctional. It is also possible to have a mixture in which the percentage of multifunctional compound is low.

The functional portions containing a labile hydrogen, may be, for example, alcohol, primary or secondary amine or thiol functions. The fourth type of compound may be a polymer terminated at the chain ends with one of these functions containing a labile hydrogen.

By way of example, when the fourth type of compound is not a polymer, mention may be made of diethylene glycol and hexaethylene glycol.

When the fourth type of compound is a polymer, mention may be made, for example, of polyethers, sulphonated polyesters and sulphonated polyamides, or a mixture of these polymers. In one embodiment, the hydrophilic block may be a polyether, such as a poly(ethylene oxide) or poly(propylene oxide).

The polymer prepared from the compounds defined above can be a cationic associative polyurethane of formula (XIX) according to the present invention. This polymer is soluble or dispersible in water and substantially increases the viscosity of the aqueous solution into which it is dissolved or dispersed.

The hydrophilic block termed Y in formula (XIX) is optional. The quaternary amine units may suffice to provide the solubility required for this type of polymer in an aqueous solution.

Oxyalkylenated Nonionic Surfactants with an HLB Value of Less Than or Equal to 5

Among these surfactants, mention may be made, in a non-limiting manner, of:

oxyethylenated alkylphenols containing not more than 2 mol of EO,

EO/PO condensates in which the EO/PO ratio is greater than 0.71, oxyethylenated plant oils containing not more than 5 mol of EO, oxyethylenated fatty alcohols containing not more than 2 mol of EO, fatty alcohols and fatty alcohol esters, for example those containing from 8 to 18 carbon atoms, fatty amides, for example those containing from 8 to 18 carbon atoms.

Anionic Surfactants

By way of a nonlimiting example of anionic surfactants which can be used, alone or as mixtures, mention may be made of salts, such as alkali metal salts, for example those chosen from sodium salts, ammonium salts, amine salts, amino alcohol salts and magnesium salts, of the following compounds: sulphates such as alkyl sulphates, alkyl ether sulphates, alkylamido ether sulphates, alkylarylpolyether sulphates, monoglyceride sulphates; sulphonates such as alkyl sulphonates, alkyl phosphates, alkylamide sulphonates, alkylaryl sulphonates, α-olefin sulphonates, paraffin sulphonates; sulphosuccinates such as ($C_6$–$C_{24}$) alkyl sulphosuccinates, ($C_6$–$C_{24}$)alkyl ether sulphosuccinates, ($C_6$–$C_{24}$)alkylamide sulphosuccinates; ($C_6$–$C_{24}$)alkyl sulphoacetates; ($C_6$–$C_{24}$)acyl sarcosinates; and ($C_6$–$C_{24}$)acyl glutamates. It is also possible to use ($C_6$–$C_{24}$)alkylpolyglycoside carboxylic esters such as alkylglucoside citrates, alkylpolyglycoside tartrates and alkylpolyglycoside sulphosuccinates; alkylsulphosuccinamates; acyl isethionates and N-acyl taurates, the alkyl or acyl radical of all of these different compounds containing, e.g., from 12 to 20 carbon atoms and the aryl radical, e.g., denoting a phenyl or benzyl group. Among the anionic surfactants which can also be used, mention may also be made of fatty acid salts such as oleic, ricinoleic, palmitic and stearic acid salts, coconut oil acid or hydrogenated coconut oil acid; acyl lactylates in which the acyl radical contains 8 to 20 carbon atoms. It is also possible to use alkyl D-galactoside uronic acids and their salts, polyoxyalkylenated ($C_6$–$C_{24}$)alkyl ether carboxylic acids, polyoxyalkylenated ($C_6$–$C_{24}$)alkylaryl ether carboxylic acids, polyoxyalkylenated ($C_6$–$C_{24}$)alkylamido ether carboxylic acids and their salts, such as those containing from 2 to 50 alkylene oxide groups such as ethylene oxide groups, and mixtures thereof.

Nonionic Surfactant(s):

Suitable nonionic surfactants include compounds such as those listed in "Handbook of Surfactants" by M. R. Porter, published by Blackie & Son (Glasgow and London), 1991, pp. 116–178). Thus, they can be chosen from, for example, polyethoxylated, polypropoxylated, alkylphenols, alphadiols and alcohols having a fatty chain containing, for example, 8 to 18 carbon atoms, it being possible for the number of ethylene oxide or propylene oxide groups to range from 2 to 50. Mention may also be made of copolymers of ethylene oxide and of propylene oxide, condensates of ethylene oxide and of propylene oxide with fatty alcohols; polyethoxylated fatty amides, such as those having from 2 to 30 mol of ethylene oxide, polyglycerolated fatty amides containing on average 1 to 5, such as 1.5 to 4, glycerol groups; polyethoxylated fatty amines such as those having 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, and amine oxides such as ($C_{10}$–$C_{14}$)alkylamine oxides and N-acylaminopropylmorpholine oxides.

Amphoteric or Zwitterionic Surfactants:

Suitable amphoteric or zwitterionic surfactants can be chosen from, for example, aliphatic secondary and aliphatic tertiary amine derivatives in which the aliphatic radical may be chosen from linear and branched chains containing from 8 to 18 carbon atoms and containing at least one water-solubilizing anionic group (for example carboxylate, sulphonate, sulphate, phosphate or phosphonate); mention may also be made of ($C_8$–$C_{20}$)alkylbetaines, sulphobetaines, ($C_8$–$C_{20}$)alkylamido($C_1$–$C_6$)alkylbetaines and ($C_8$–$C_{20}$) alkylamido($C_1$–$C_6$)alkylsulphobetaines.

Among the amine derivatives, mention may be made of the products sold under the name Miranol®, as described in U.S. Pat. Nos. 2,528,378 and 2,781,354, and classified in the CTFA dictionary, 3rd edition, 1982, under the names Amphocarboxyglycinates and Amphocarboxypropionates, with the respective structures:

in which:

$R_2$ may be chosen from alkyl radicals of an acid $R_2$—COOH present in hydrolyzed coconut oil, heptyl radicals, nonyl radicals, and undecyl radicals, $R_3$ may be a beta-hydroxyethyl group, $R_4$ may be a carboxymethyl group; and

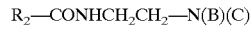

in which:

B may be —$CH_2CH_2OX'$,

C may be —$(CH_2)_{z'}$—Y', with z'=1 or 2,

X' may be chosen from a —$CH_2CH_2$—COOH group and hydrogen,

Y' may be chosen from —COOH and a —$CH_2$—CHOH—$SO_3H$ radical, $R_2$ may be chosen from alkyl radicals of an acid $R_9$—COOH present in coconut oil and hydrolyzed linseed oil, alkyl radicals, such as a $C_7$, $C_9$, $C_{11}$ and $C_{13}$ alkyl radical, a $C_{17}$ alkyl radical and its iso form, and an unsaturated $C_{17}$ radical.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphopropionate, Disodium Caprylamphodipropionate, Disodium Caprylamphodipropionate, Lauroamphodipropionic acid and Cocoamphodipropionic acid.

By way of example, mention may be made of the cocoamphodiacetate sold under the trade name Miranol® C2M concentrate by the company Rhodia Chimie.

Cationic Surfactants:

Among the suitable cationic surfactants, mention may be made, for example, of: salts of optionally polyoxyalkylenated primary, secondary or tertiary fatty amines; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

The aqueous hydrogen peroxide composition may contain at least one stabilizer chosen from, for example, alkali metal and alkaline-earth metal pyrophosphates, alkali metal and alkaline-earth metal stannates, phenacetin and oxyquinoline acid salts, for instance oxyquinolenic sulphate. More advantageously, use may be made of at least one stannate optionally in combination with at least one pyrophosphate.

In one embodiment, the aqueous hydrogen peroxide composition may have a pH of less than 7. The acidic pH may ensure that the hydrogen peroxide is stable in the composition.

This acidic pH may be obtained with the aid of acidifying agents such as, for example, hydrochloric acid, acetic acid, ethydronic acid, phosphoric acid, lactic acid or boric acid, and it may be adjusted conventionally by adding either basifying agents such as, for example, aqueous ammonia, monoethanolamine, diethanolamine, triethanolamine, isopropanolamine, 1,3-diaminopropane, an ammonium or alkali metal (bi)carbonate, an organic carbonate such as guanidine carbonate, or alternatively an alkali metal hydroxide, it being possible, of course, for all these compounds to be taken alone or as a mixture.

The aqueous hydrogen peroxide composition may also contain preserving agents, colorants, fragrances, antifoams and sequestering agents such as, for example, ethylenediaminetetraacetic acid (EDTA) or Pentasodium Pentetate (CTFA name).

These optional additional compound(s) mentioned above are such that the advantageous properties intrinsically associated with the pulverulent bleaching composition or the ready-to-use bleaching composition according to the invention are not, or are not substantially, adversely affected by the envisaged addition(s).

The pH of the ready-to-use bleaching composition generally may range from 4 to 12. The pH may, for example, range from 7 to 11.5, such as from 8 to 11.

In one embodiment, the bleaching method comprises mixing, at the time of application, a pulverulent composition as described previously with an aqueous hydrogen peroxide composition having a titre of not more than 40 volumes to produce a bleaching composition and applying the bleaching composition to the keratin fibers; leaving the bleaching composition on the fibers for an exposure time ranging from 1 to 60 minutes, for example, from 10 to 45 minutes; rinsing the fibers; and optionally, washing the rinsed fibers with shampoo, rinsing the washed fibers, and drying the rinsed fibers.

Another aspect of the present invention comprises a multi-compartment device, or "kit", for bleaching human keratin fibers, such as hair. The device comprises at least two compartments, one of which contains a pulverulent composition as described above, and the other of which contains an aqueous hydrogen peroxide composition having a titre of not more than 40 volumes.

Another aspect of the present invention provides a method for preparing the pulverulent composition, mixing, at ambient temperature, such as, for example, 25° C., at least one fatty acid sugar ester as described above, with a mixture comprising at least one peroxygenated salt and at least one polymer chosen from nonionic and anionic amphiphilic polymers, wherein said at least one polymer comprises at least one fatty chain. The method can further comprise adding alkaline agent and various other adjuvants.

Concrete examples illustrating the invention are given below, without, however, having any limiting nature.

EXAMPLE 1

The anhydrous, non-volatile pulverulent composition below for bleaching the hair (A) was prepared (amounts expressed in grams):

| | |
|---|---|
| Potassium persulphate | 48 |
| Sodium persulphate | 8 |
| Sodium metasilicate | 12 |
| Ammonium chloride | 4.5 |
| Magnesium oxide | 1 |
| Urea | 4 |
| EDTA (sequestering agent) | 1 |
| Clay | 4.5 |
| Fatty-chain nonionic amphiphilic polymer: Ser-ad FX 1100 sold by the company Servo Delden | 3 |
| Fatty-chain nonionic amphiphilic polymer: Jaguar XC-95/3 sold by the company Rhodia | 1 |
| Water-soluble thickening polymer: Sodium alginate | 2 |
| Anionic surfactant: Sodium cetostearyl sulphate | 3 |
| Calcium stearate | 2 |
| Titanium oxide | 2 |
| Colorant | 0.2 |
| Methylglucose dioleate sold under the name Glucate DO by the company Amerchol | 2 |

1. Assessment of the Stability on Storage of a Sample of Composition (A)

The stability on storage over time of a sample of composition A above was assessed, by measuring the content of sodium persulphate and potassium persulphate of the composition, before and after 2 months of storage at 45° C. (T1 and T2, respectively). (These accelerated storage conditions make it possible to predict the stability of the sample under normal storage conditions.)

The content of sodium persulphate and of potassium persulphate is expressed in meq/g, and was determined by redox potential assay, in acidic medium and in the presence of ferrous sulphate, using a potassium permanganate solution.

The loss of sodium persulphate and of potassium persulphate after 2 months at 45° C. (P) was thus determined by means of the following calculation:

$(P)=100*[(T1-T2)/T1]$

When this loss (P) is less than 5%, it is considered that the sample will have good stability under normal storage conditions.

The stability on storage of sample (A) was thus studied after 2 months at 45° C.; the results were as follows:

| | T1 (content before storage for 2 months at 45° C.) | T2 (content after storage for 2 months at 45° C.) | Loss of persulphates |
|---|---|---|---|
| Sample (A) | 4.16 meq/g | 4.09 meq/g | 1.6% |

It is concluded therefrom that the pulverulent composition (A) according to the invention shows very good stability on storage.

2. Measurement of the Particle Size of Composition (A)

A particle size measurement was performed on a sample of composition (A) using a Retsch AS 200 Digit granulometer (oscillation height: 1.25 mm/screening time: 5 minutes).

| Diameter of the screens in microns | Particles retained by the corresponding screen, in % |
|---|---|
| 800 microns | 1% |
| 400 microns | 30.5% |
| 200 microns | 57.5% |
| 125 microns | 10.5% |
| 63 microns | 0.5% |
| 32 microns | 0% |
| Bottom | 0% |

Composition (A) according to the invention contains no fine particles with a diameter of less than 63 microns.

3. Mixing Before Use of Composition (A) with a Stabilized Aqueous Hydrogen Peroxide Composition Two mixtures prepared were compared before use:
that of composition (A) with a stabilized aqueous 30-volumes (9%) hydrogen peroxide composition (B), in accordance with the invention, with
that of the same composition (A) with a stabilized aqueous hydrogen peroxide composition (Ba) not formulated for cosmetic use (110 volumes), not in accordance with the invention.

Compositions (B) and (Ba) are given below:
(amounts expressed in grams %)

| | Composition (B) | Composition (Ba) |
|---|---|---|
| 50% hydrogen peroxide | 18 (30 vol) | 66 (110 vol) |
| Nonionic surfactant of HLB = 1: Cetostearyl alcohol | 2.5 | |
| Nonionic surfactant of HLB = 2: Trideceth-2 carboxamide MEA | 0.8 | |
| Nonionic surfactant: 30 EO oxyethylenated cetostearyl alcohol | 0.6 | |
| Pentasodium pentetate (sequestering agent) | 0.05 | |
| Tetrasodium pyrophosphate | 0.03 | |
| Sodium stannate | 0.02 | |
| 85% phosphoric acid | 0.4 | |
| Water qs | 100 | 100 |

Mixtures (A)(B) and (A)(Ba) were prepared by mixing 30 g of the non-volatile pulverulent composition (A) with 45 g of the stabilized aqueous hydrogen peroxide composition (B) or (Ba).

4. Results:

Each mixture (A)(B) and (A)(Ba) was applied to hair to bleach it.

The mixture (A)(Ba) was heterogeneous and unstable. It did not allow an easy or sufficiently precise application without running, and spread onto the areas of the hair that were not intended to be bleached. It gave a heterogeneous hair bleaching effect, leaving the hair coarse.

The mixture (A)(B) was homogeneous, easy to apply and thick enough to allow a precise application to the areas of the hair that were intended to be bleached. It gave a powerful and homogeneous hair bleaching effect while at the same time leaving the hair much less coarse than with the mixture (A)(Ba).

It was also found that composition (A) allowed larger dilutions, with the stabilized aqueous hydrogen peroxide composition (B) according to the invention than with the aqueous hydrogen peroxide composition (Ba) not formulated for cosmetic use.

EXAMPLE 2

1. The pulverulent, anhydrous, non-volatile hair bleaching compositions (C), (D), (E), (F) and (G) below were prepared:

(amounts expressed in grams)

| COMPOSITIONS → | (C) | (D) | (E) | (F) | (G) |
|---|---|---|---|---|---|
| Potassium persulphate | 35 | 37.5 | 39.5 | 36 | 20 |
| Sodium persulphate | 10 | 5 | 5 | | 20 |
| 20% Magnesium peroxide | | 2 | | 1.9 | 4.3 |
| Sodium disilicate | 12 | 24 | 25 | 22 | 25 |
| Sodium metasilicate | 12 | 1.3 | | 2 | |
| Ammonium chloride | 3 | 2.5 | 2.5 | 2 | 4 |
| Magnesium carbonate | 5 | | | 4 | 1.5 |

-continued

| COMPOSITIONS → | (C) | (D) | (E) | (F) | (G) |
|---|---|---|---|---|---|
| Magnesium oxide | | | 0.3 | | |
| Urea | 3 | 4 | 2 | 3 | |
| EDTA (sequestering agent) | 1 | 0.5 | 0.5 | 0.5 | 1 |
| Colloidal silica | | | | | 0.5 |
| Fumed silica of hydrophilic nature | 2.5 | | | | |
| Fumed silica of hydrophobic nature | | | | 2.7 | |
| Clay | 3 | 4 | 4 | 3 | 3 |
| Fatty-chain nonionic amphiphilic polymer: Ser-ad FX 1100 from the company Servo Delden | 3 | | | | 2 |
| Fatty-chain nonionic amphiphilic polymer: Jaguar XC-95/3 from the company Rhodia | 2.8 | | 1 | | 2 |
| Fatty-chain anionic amphiphilic polymer: Carbopol ETD2020 from the company Goodrich | | 5 | 4 | 5 | |
| Fatty-chain anionic amphiphilic polymer: Carbopol 1382 from the company Goodrich | | | | | 2 |
| Water-soluble thickening polymer: unmodified nonionic guar gum (Guargel D/15 from the company Goodrich) | 2 | | | | 1.7 |
| Water-soluble thickening polymer: Primogel from the company Avebe | | 3 | 3 | 0.5 | |
| Sodium lauryl sarcosinate | 2 | | | | 0.5 |
| Sodium cetostearyl sulphate | 1 | 2 | 2 | 2 | 3 |
| Magnesium stearate | 3 | 3 | | 2 | |
| Calcium stearate | | | 3 | | 2 |
| Polyvinylpyrrolidone | 2 | 2.8 | 3 | 2 | 2 |
| Titanium oxide | 2 | 1 | 1 | 1 | 2 |
| Colorant | | 0.2 | | | 0.5 |
| Amphoteric conditioning polymer: Polyquaternium-22 | 0.2 | | 0.2 | | 0.5 |
| Fragrance | | 0.2 | | 0.5 | |
| Methylglucose dioleate sold under the name Glucate DO by the company Amerchol | 9.5 | 2 | 2 | 9.9 | 2.5 |

2. The stabilized aqueous hydrogen peroxide compositions (H), (I), (J), (K) and (L) below were also prepared:
(amounts expressed in grams)

| COMPOSITIONS → | (H) | (I) | (J) | (K) | (L) |
|---|---|---|---|---|---|
| 50% Hydrogen peroxide | 18 (30 vol) | 24 (40 vol) | 18 (30 vol) | 12 (20 vol) | 18 (30 vol) |
| Nonionic surfactant of HLB = 1 Cetostearyl alcohol | | | | 2 | 1 |
| Nonionic surfactant of HLB = 1 Cetyl alcohol | | | | 1 | 3 |
| Nonionic surfactant of HLB = 5: 2 EO oxyethylenated cetyl alcohol | 1.1 | | | | |
| Nonionic surfactant: 30 EO oxyethylenated cetostearyl alcohol | 3 | | 0.5 | | 1 |
| Nonionic surfactant: 10 EO oxyethylenated cetyl alcohol | 2.2 | | 0.7 | | |
| Anionic surfactant: Sodium cetearyl sulphate | | | | 0.5 | |
| Anionic surfactant: Sodium lauryl sulphate | | | | 0.2 | |
| Anionic surfactant: Sodium (C14/C16)olefin sulphonate | | | 0.1 | 0.3 | 1 |
| Anionic surfactant: Sodium cocoyl isethionate | | | 0.1 | | |
| Fatty-chain anionic amphiphilic polymer: Aculyn 22 from the company Rohm & Haas | 2 | | | | |
| Water-soluble thickening polymer: Simulgel EG from the company SEPPIC | | 2 | | | |
| Water-soluble thickening polymer: Hostacerin AMPS from the company Clariant | | 3 | | | |
| Disodium phosphate | | | 0.08 | | 0.05 |

-continued

| COMPOSITIONS → | (H) | (I) | (J) | (K) | (L) |
|---|---|---|---|---|---|
| Pentasodium pentetate (sequestering agent) | 0.05 | | | 0.06 | |
| Tetrasodium pyrophosphate | 0.03 | 0.04 | 0.03 | 0.04 | 0.02 |
| Sodium stannate | 0.01 | 0.02 | 0.02 | / | 0.02 |
| Fragrance | | | 1 | 0.5 | |
| Antifoam: Simethicone | | | 0.5 | 0.6 | |
| Ethydronic acid qs pH | | 3.5 | | 2.5 | |
| 85% Phosphoric acid qs pH | 3 | | 2.5 | | 2 |
| Demineralized water | | | qs 100 | | |

3. The ready-to-use bleaching compositions (C)(H), (D)(L), (E)(J), (F)(K) and (G)(I) below were then prepared:
  30 g of the pulverulent composition (C)+60 g of the hydrogen peroxide composition (H),
  30 g of the pulverulent composition (D)+40 g of the hydrogen peroxide composition (L),
  30 g of the pulverulent composition (E)+45 g of the hydrogen peroxide composition (J),
  30 g of the pulverulent composition (F)+40 g of the hydrogen peroxide composition (K),
  30 g of the pulverulent composition (G)+40 g of the hydrogen peroxide composition (I).

The ready-to-use bleaching compositions thus obtained and in accordance with the invention were homogeneous, easy to apply and thick enough to allow a precise application to the areas of the hair that were intended to be bleached. They gave powerful and homogeneous bleaching effects, while at the same time not leaving the hair coarse.

For comparative purposes, ready-to-use bleaching compositions (C)(Ba), (D)(Ba), (E)(Ba), (F)(Ba) and (E)(Ba) which were prepared from 30 g of each of the pulverulent compositions (C) or (D) or (E) or (F) or (G) with 30 g of the hydrogen peroxide composition (Ba) described in paragraph 3 of Example 1, were heterogeneous and too unstable. They did not allow an easy and sufficiently precise application without running, and they spread onto the areas of the hair that were not intended to be bleached. They gave heterogeneous hair bleaching effects and left the hair coarse.

In addition, it was found that the pulverulent bleaching compositions (C), (D), (E), (F) and (G) were non-volatile and stable on storage. In addition, they allowed much larger dilutions with the stabilized aqueous hydrogen peroxide compositions (H), (I), (J), (K) and (L) in accordance with the invention, than with the aqueous hydrogen peroxide composition (Ba) not formulated for cosmetic use.

What is claimed is:

1. A method of preparing a ready-to-use composition for bleaching human keratin fibers, comprising:
  mixing, at the time of application, a pulverulent composition with an aqueous hydrogen peroxide composition having a hydrogen peroxide titre of not more than 40 volumes, the pulverulent composition comprising, in a medium that is suitable for bleaching:
    at least one peroxygenated salt;
    at least one amphiphilic polymer chosen from nonionic amphiphilic and anionic amphiphilic polymers, the at least one amphiphilic polymer comprising at least one fatty chain; and
    at least one fatty acid sugar ester comprising at least one sugar residue and at least one $C_{12}$–$C_{24}$ fatty acid residue, the at least one fatty acid sugar ester being present and in an amount of less than 10% by weight relative to the total weight of the composition.

2. The method according to claim 1, wherein the human keratin fibers are hair.

3. The method according to claim 1, wherein the hydrogen peroxide titre of the aqueous hydrogen peroxide composition ranges from 2 to 40 volumes.

4. The method according to claim 1, wherein the aqueous hydrogen peroxide composition further comprises at least one ingredient chosen from:
  (i) at least one surfactant chosen from anionic and nonionic surfactants, the at least one surfactant being present in an amount ranging from 0.1% to 10% by weight relative to the total weight of the aqueous hydrogen peroxide composition;
  (ii) a combination of at least two nonionic surfactants with different HLB values, at least one of which is less than 5, the combination being present in a total amount ranging from 1.5% to 40% by weight relative to the total weight of the aqueous hydrogen peroxide composition;
  (iii) a combination of at least one nonionic surfactant with an HLB value of less than or equal to 5, and at least one anionic surfactant, the combination being present in a total amount ranging from 1% to 30% by weight relative to the total weight of the aqueous hydrogen peroxide composition; and
  (iv) at least one thickening polymer present in an amount ranging from 0.1% to 10% by weight relative to the total weight of the aqueous hydrogen peroxide composition.

5. The method according to claim 4, wherein the aqueous hydrogen peroxide composition comprises the at least one surfactant (i) in an amount ranging from 0.1% to 5% by weight relative to the total weight of the aqueous hydrogen peroxide composition.

6. The method according to claim 4, wherein the aqueous hydrogen peroxide composition comprises the combination (ii) of at least two nonionic surfactants in a total amount ranging from 1.5% to 20% by weight relative to the total weight of the aqueous hydrogen peroxide composition.

7. The method according to claim 4, wherein the aqueous hydrogen peroxide composition comprises the combination (iii) of at least one nonionic surfactant and at least one anionic surfactant in a total amount ranging from 1.5% to 15% by weight relative to the total weight of the aqueous hydrogen peroxide composition.

8. The method according to claim 4, wherein the aqueous hydrogen peroxide composition comprises the at least one thickening polymer (iv) in combination with at least one surfactant in an amount ranging from 0.1% to 10% by weight relative to the total weight of the aqueous hydrogen peroxide composition.

9. The method according to claim 8, wherein the at least one thickening polymer (iv) is combined with the at least one surfactant in an amount ranging from 0.1% to 5% relative to the total weight of the aqueous hydrogen peroxide composition.

10. The method according to claim 4, wherein the aqueous hydrogen peroxide composition comprises the at least one thickening polymer in an amount ranging from 0.1% to 5% by weight relative to the total weight of the aqueous hydrogen peroxide composition.

11. A method of bleaching human keratin fibers, comprising:
  mixing, at the time of application, a pulverulent composition with an aqueous hydrogen peroxide composition having a titre of not more than 40 volumes to produce a bleaching composition, the pulverulent composition comprising, in a medium that is suitable for bleaching:
    at least one peroxygenated salt;
    at least one amphiphilic polymer chosen from nonionic amphiphilic and anionic amphiphilic polymers, the at least one amphiphilic polymer comprising at least one fatty chain, and
    at least one fatty acid sugar ester comprising at least one sugar residue and at least one $C_{12}$–$C_{24}$ fatty acid residue, the at least one fatty acid sugar ester being present and in an amount of less than 10% by weight relative to the total weight of the composition;
  applying the bleaching composition to the keratin fibers, and
  leaving the bleaching composition on the fibers for an exposure time sufficient to bleach the fibers.

12. The method according to claim 11, wherein the human keratin fibers are hair.

13. The method according to claim 11, wherein the exposure time ranges from 1 to 60 minutes.

14. The method according to claim 13, wherein the exposure time ranges from 10 to 45 minutes.

15. The method according to claim 11, further comprising rinsing the bleached fibers.

16. The method according to claim 15, further comprising washing the rinsed fibers with shampoo, rinsing the washed fibers, and drying the rinsed fibers.

17. A kit for bleaching human keratin fibers comprising at least two compartments, wherein:
  a first compartment comprises a pulverulent composition comprising, in a medium that is suitable for bleaching:
    at least one peroxygenated salt;
    at least one amphiphilic polymer chosen from nonionic amphiphilic and anionic amphiphilic polymers, the at least one amphiphilic polymer comprising at least one fatty chain, and
    at least one fatty acid sugar ester comprising at least one sugar residue and at least one $C_{12}$–$C_{24}$ fatty acid residue, the at least one fatty acid sugar ester being present and in an amount of less than 10% by weight relative to the total weight of the composition; and
  a second compartment comprises an aqueous hydrogen peroxide composition having a hydrogen peroxide titre of not more than 40 volumes.

18. The kit according to claim 17, wherein the human keratin fibers are hair.

19. A method of preparing a pulverulent composition for bleaching human keratin fibers, comprising:
  mixing, at a temperature of 25° C.:
    at least one fatty acid sugar ester comprising at least one sugar residue and at least one $C_{12}$–$C_{24}$ fatty acid residue, the at least one fatty acid sugar ester being present and in an amount of less than 10% by weight relative to the total weight of the composition, with
    a mixture comprising at least one peroxygenated salt and at least one amphiphilic polymer chosen from nonionic amphiphilic and anionic amphiphilic polymers, the at least one amphiphilic polymer comprising at least one fatty chain.

20. The method according to claim 19, wherein the human keratin fibers are hair.

21. A ready-to-use composition for bleaching human keratin fibers, comprising:
  a pulverulent composition comprising, in a medium that is suitable for bleaching:
    at least one peroxygenated salt;
    at least one amphiphilic polymer chosen from nonionic amphiphilic and anionic amphiphilic polymers, the at least one amphiphilic polymer comprising at least one fatty chain; and
    at least one fatty acid sugar ester comprising at least one sugar residue and at least one $C_{12}$–$C_{24}$ fatty acid residue, the at least one fatty acid sugar ester being present and in an amount of less than 10% by weight relative to the total weight of the composition; and
  an aqueous hydrogen peroxide composition having a hydrogen peroxide titre of not more than 40 volumes.

* * * * *